US009683246B2

(12) United States Patent
Mohammed et al.

(10) Patent No.: US 9,683,246 B2
(45) Date of Patent: *Jun. 20, 2017

(54) REAGENTS AND METHODS FOR CYANOBACTERIAL PRODUCTION OF BIOPLASTICS AND BIOMATERIALS

(71) Applicant: Arizona Board of Regents, A Body Corporate Acting for and on Behalf of Arizona State University, Scottsdale, AZ (US)

(72) Inventors: Hatem Mohammed, Corvallis, OR (US); Willem Vermaas, Tempe, AZ (US)

(73) Assignee: Arizona Board of Regents, A Body Corporate Acting For And On Behalf of Arizona State University, Scottsdale, AZ (US)

( * ) Notice: Subject to any disclaimer, the term of this patent is extended or adjusted under 35 U.S.C. 154(b) by 146 days.

This patent is subject to a terminal disclaimer.

(21) Appl. No.: 14/603,235

(22) Filed: Jan. 22, 2015

(65) Prior Publication Data

US 2015/0140622 A1     May 21, 2015

Related U.S. Application Data

(60) Continuation of application No. 13/911,814, filed on Jun. 6, 2013, now Pat. No. 8,962,300, which is a division of application No. 12/664,433, filed as application No. PCT/US2008/068623 on Jun. 27, 2008, now Pat. No. 8,465,965.

(60) Provisional application No. 60/937,400, filed on Jun. 27, 2007.

(51) Int. Cl.
*C12P 7/62* (2006.01)
*C12N 1/21* (2006.01)
*C12N 9/12* (2006.01)
*C12N 9/00* (2006.01)

(52) U.S. Cl.
CPC ............ *C12P 7/625* (2013.01); *C12N 9/1205* (2013.01); *C12N 9/93* (2013.01); *C12Y 207/01023* (2013.01); *C12Y 603/05001* (2013.01)

(58) Field of Classification Search
CPC ......... C12N 9/1205; C12N 9/93; C12P 7/625; C12Y 207/01023; C12Y 603/05001
See application file for complete search history.

(56) References Cited

U.S. PATENT DOCUMENTS

| 5,107,065 | A  | 4/1992 | Shewmaker et al. |
| 5,231,020 | A  | 7/1993 | Jergensen et al. |
| 2002/0115141 | A1 | 8/2002 | Ziegler et al. |
| 2002/0164706 | A1 | 11/2002 | Huang et al. |
| 2002/0169562 | A1 | 11/2002 | Stephanopoulos et al. |
| 2003/0233675 | A1 | 12/2003 | Cao et al. |
| 2004/0157331 | A1 | 8/2004 | Van Dyk et al. |

FOREIGN PATENT DOCUMENTS

DE      19813692 A1    9/1999

OTHER PUBLICATIONS

Sousa et al., Microbiology 148(Pt5):1291-1303, 2002.*
Mes, Ted H.M., et al., "Variable selection pressures across lineages in Trichodesmium and related cyanobacteria based on the heterocyst differentiation protein gene hetR," Gene, Feb. 2005, pp. 163-171, vol. 346.
Mes, Ted H.M., et al., "Positive selection on transposase genes of insertion sequences in the Crocosphaera watsonii genome," J. Bacteriol., Oct. 2006, pp. 7176-7185, vol. 188, No. 20.
Kokshaova, Olga A., et al., "Genetic tools for cyanobacteria," Appl. Microbiol. Biotechnol., Feb. 2002, pp. 123-137, vol. 58, No. 2.
Golden, Susan S., "Mutagenesis of cyanobacteria by classical and gene-transfer-based methods," Methods Enzymol., 1988, pp. 714-727, vol. 167.
Taroncher-Oldenburg, Gaspar, et al., "Identification and analysis of the polyhydroxyalkanoate-specific beta-ketothiolase and acetoacetyl coenzyme A reductase genes in the Cyanobacterium synechocystis sp. strain PCC6803," Appl. Environ. Microbiol., Oct. 2000, pp. 4440-4448, vol. 66, No. 10.
Hein, Silke, et al., "*Synechocystis* sp. PCC6803 possesses a two-component polyhydroxyalkanoic acid synthase similar to that of anoxygenic purple sulfur bacteria," Arch. Microbiol., Sep. 1998, pp. 162-170, vol. 170, No. 3.
Briggs, Linda M., et al., "Copper-induced expression, cloning, and regulatory studies of the plastocyanin gene from the Cyanobacterium *synechocystis* sp. PCC 6803," Plant Mol. Biol., Oct. 1990, pp. 633-642, vol. 15, No. 4.
Danner, Robert L., et al., "Purification, toxicity, and antiendotoxin activity of polymyxin B nonapeptide," Antimicrob. Agents Chemother., Sep. 1989, pp. 1428-1434, vol. 33, No. 9.
Duhring, Ulf, et al., "An internal antisense RNA regulates expression of the photosynthesis gene isiA," Proc. Natl. Acad. Sci. U.S.A., May 2006, pp. 7054-7058, vol. 103, No. 18.
Mohamed, Hatem E., et al., "Myxoxanthophyll is required for normal cell wall structure and thylakoid organization in the *Cyanobacterium synechocystis* sp. strain PCC 6803," J. Bacteriol., Oct. 2005, pp. 6883-6892, vol. 187, No. 20.
Mohamed, Hatem E., et al., "SII0254 (CrtLdiox) is a Bifunctional Lycopene Cyclase/Dioxygenase in Cyanobacteria Producing Myxoxanthophyll," J. Bacteriol., May 2006, pp. 3337-3344, vol. 188, No. 9.
Mohamed, Hatem E., et al., "Slr1293 in *Synechocystis* sp. Strain PCC 6803 Is the C-3',4' Desaturase (CrtD) Involved in Myxoxanthophyll Biosynthesis," J. Bacteriol., Sep. 2004, pp. 5621-5628, vol. 186, No. 17.
Sara, et al., "S-layers as patterning elements for application in nanobiotechnology," J. Nanosci. Nanotechnol., Dec. 2005, pp. 1939-1953, vol. 5, No. 12.

(Continued)

*Primary Examiner* — Delia Ramirez
(74) *Attorney, Agent, or Firm* — McDonnell Boehnen Hulbert & Berghoff LLP

(57) ABSTRACT

The present invention provides reagents and methods for biomaterial production from cyanobacteria.

10 Claims, 4 Drawing Sheets

(56) References Cited

OTHER PUBLICATIONS

Yu, Jian et al., "Cost-effective recovery and purification of polyhydroxyalkanoates by selective dissolution of cell mass," Biotechnol. Prog., Mar.-Apr. 2006, pp. 547-553, vol. 22, No. 2.

He, Qingfang, et al.. "Chlorophyll alpha synthesis upon interruption and deletion of por coding for the light-dependent NADPH: protochlorophyllide oxidoreductase in a photosystem-I-less/chIL-strain of *Synechocystis* sp. PCC 6803," Eur. J. Biochem., Apr. 1998, pp. 161-172, vol. 253, No. 1.

Kaneko, Takakazu, et al., "Sequence Analysis of the Genome of the Unicellular *Cyanobacterium synechocystis* sp. Strain PCC6803. II. Sequence Determination of the Entire Genome and Assignment of Potential Protein-coding Regions," DNA Res., Jun. 1996, pp. 109-136, vol. 3, No. 3.

Law, John H., et al., "Assay of poly-beta-hydroxybutyric acid," J. Bacteriol., Jul. 1961, pp. 33-36, vol. 82, No. 1.

Rippka, Rosmarie, et al., "Generic Assignments, Strain Histories and Properties of Pure Cultures of Cyanobacteria," J. Gen. Microbiol., Mar. 1979, pp. 1-61, vol. 111, No. 1.

Vermaas, Wim F.J., et al., "Sequencing and modification of psbB, the gene encoding the CP-47 protein of Photosystem II, in the cyanobacterium Synechocystis 6803," Plant Mol. Biol., 1987, pp. 317-326, vol. 8, No. 4.

Gerdes, Svetlana Y., et al., "Comparative Genomics of NAD Biosynthesis in Cyanobacteria," J. Bacteriol., Apr. 2006, pp. 3012-3023, vol. 188, No. 8.

Rusch, Douglas B., et al., "The Sorcerer II Global Ocean Sampling Expedition: Northwest Atlantic through Eastern Tropical Pacific," PLoS Biol., Mar. 2007, p. e77, vol. 5, No. 3.

Zhang, Shulu, et al., "Four Novel Genes Required for Optimal Photoautotrophic Growth of the *Cyanobacterium synechocystis* sp. Strain PCC 6803 Identified by In vitro Transposon Mutagenesis," J. Bacteriol., Feb. 2004, pp. 875-879, vol. 186. No. 3.

International Search Report and Written Opinion for PCT US2008/068623 mailed Dec. 19, 2008 (19 pages).

International Preliminary Report on Patentability for PCT US2008/068623 mailed Jan. 14, 2010 (13 pages).

Branch, A., TIBS 23:45-50, 1998; A good antisense molecule is hard to find.

\* cited by examiner

2-Cyanophycin production

3-Hydroxybutyrate production.

US 9,683,246 B2

REAGENTS AND METHODS FOR CYANOBACTERIAL PRODUCTION OF BIOPLASTICS AND BIOMATERIALS

CROSS REFERENCE

This application is a continuation of U.S. application Ser. No. 13/911,814 filed Jun. 6, 2013, which is a divisional application of Ser. No. 12/664,433 filed Mar. 24, 2010, now U.S. Pat. No. 8,465,965 issued Jun. 18, 2013, which claims priority under 35 USC 371 of PCT application serial number PCT/US2008/068623 filed Jun. 27, 2008, which claims priority to U.S. Patent Application Ser. No. 60/937,400 filed Jun. 27, 2007, incorporated by reference herein in its entirety.

BACKGROUND OF THE INVENTION

In the coming decades, renewables are expected to gradually replace petrochemical-based industrial products, including polymers. Production of plastics from biopolymers offers the potential to replace non-renewable materials derived from petroleum with renewable resources, resulting in reliable (domestic) supplies, jobs in rural communities, sustainable production, lower greenhouse gas production, and competitive prices.

In response to an increased awareness of global environmental problems, PHA (Polyhydroxyalkanoates (PHA)) is gaining serious attention as a potential substitute for non-biodegradable polymers. The current rise of the oil and natural gas prices is reflected in the plastics market, and is making renewable bioplastics more competitive. However, prices of raw materials for the production of bioplastics based on bacterial fermentation are also increasing.

According to some reports, the cost of production of bioplastics by bacterial fermentation, especially when energy and materials consumed for the production of fertilizers, pesticides, transport, and process energy are factored in, is higher than that of photosynthetically produced plastics, for which no raw material and fossil-fuel energy is required and that take up $CO_2$ from the environment. Thus, biopolymers produced from autotrophic cyanobacteria that generate their own fixed-carbon sources are likely to have an ever-increasing advantage over the production of biopolymers by fermentation.

SUMMARY OF THE INVENTION

In one aspect, the present invention provides methods for producing biomaterials, comprising:
 (a) culturing cyanobacterial host cells that are deficient in Slr1125 expression;
 (b) harvesting the cyanobacterial host cells; and
 (c) preparing biomaterials from the harvested cyanobacterial host cells.

The methods of the invention can be used, for example, to produce quantities of biomaterials not previously possible using known cyanobacterial host cells. In one embodiment the cyanobacterial host cells have been genetically engineered to reduce or eliminate Slr1125 expression. In another embodiment, the biomaterials comprise biomaterials selected from the group consisting of polyhydroxyalkanoates (PHA) and cyanophycin. In a further embodiment, the cyanobacterial host cells are selected from the group consisting of *Synechocystis, Arthrospira maxima, Synechococcus, Trichodesmium*; and *Crocosphaera*. In another embodiment, the cyanobacterial host cells are *Synechocystis* sp. PCC 6803 cells. In various further embodiments, the cyanobacterial host cells have been recombinantly engineered to delete the slr1125 gene; the cyanobacterial host cells have been genetically engineered to overexpress NAD synthetase and/or NAD+ kinase; the cyanobacterial host cells are deficient in cyanophycin production; the cyanobacterial host are deficient in expression of Slr1993; the cyanobacterial host cells are deficient in cyanophycinase expression, and the cyanobacterial host cells are recombinantly engineered to reduce or eliminate expression of one or more of Slr1994, Slr1829, and Slr1830.

In a further aspect, the present invention comprises isolated recombinant nucleic acids, comprising:
 (a) a first nucleic acid comprising an inducible cyanobacterial promoter; and
 (b) a second nucleic acid operably linked to the first nucleic acid, wherein the second nucleic acid encodes an inhibitory nucleic acid complementary to a target nucleic acid sequence that encodes an amino acid sequence of a polypeptides selected from the group consisting of SEQ ID NO:2, SEQ ID NO:4, SEQ ID NO:6, and SEQ ID NO:8. The isolated nucleic acids of the invention can be used, for example, to down-regulate expression of Slr1125 in cyanobacterial cells, which is useful, for example, in producing biomaterials according to the methods of the present invention. In one embodiment, the inhibitory nucleic acid comprises and antisense nucleic acid. In another embodiment, the target nucleic acid sequence is selected from the group consisting of SEQ ID NO:1, SEQ ID NO:3, SEQ ID NO:5, and SEQ ID NO:7. In a further embodiment, the inducible cyanobacterial promoter comprises SEQ ID NO:9. In a further embodiment, the isolated nucleic acid further comprises a third nucleic acid that encodes an NAD synthetase protein selected from the group consisting of SEQ ID NO:10, 11, and 12. In another embodiment, the third nucleic acid consists of a NAD synthetase coding sequence according to SEQ ID NO:13, 14, or 15. In another embodiment, the isolated nucleic acids of the invention are provided in a vector for replication and expression.

In another aspect, the present invention provides recombinant host cells comprising isolated nucleic acids or expression vectors according to the invention. Such host cells can be used, for example, to produce large amounts of the isolated nucleic acids of the invention, of to carry out the methods of the invention. In one embodiment, the host cell is a cyanobacterial host cell; in another embodiment, the recombinant host cell is a bacterial host cell. In a further embodiment, the recombinant cyanobacterial host cell is selected from the group consisting of *Synechocystis, Arthrospira maxima, Synechococcus, Trichodesmium*; and *Crocosphaera*. In another embodiment, the recombinant cyanobacterial host cell is a *Synechocystis* PCC 6803 cell. In a further embodiment, the recombinant nucleic acid is chromosomally integrated into the cyanobacterial genome. In various further embodiments, the cyanobacterial host cells have been recombinantly engineered to delete the slr1125 gene; the cyanobacterial host cells have been genetically engineered to overexpress NAD synthetase and/or NAD+ kinase; the cyanobacterial host cells are deficient in cyanophycin production; the cyanobacterial host are deficient in expression of Slr1993; the cyanobacterial host cells are deficient in cyanophycinase expression, and the cyanobacterial host cells are recombinantly engineered to reduce or eliminate expression of one or more of Slr1994, Slr1829, and Slr1830.

In a further aspect, the present invention provides recombinant cyanobacterial host cell, comprising:

(a) a deficiency in Slr1125 expression; and
(b) one or more of the following recombinantly generated phenotypes:
  (i) a deficiency in cyanophycin production;
  (ii) a deficiency in poly-β-hydroxyalkanoate (PHA) production;
  (iii) overexpression of NAD synthetase;
  (iv) overexpression of NAD+ kinase;
  (v) deficiency in cyanophycin synthetase expression;
  (vi) deficiency in Slr1993 expression;
  (vii) deficiency in cyanophycinase expression;
  (viii) deficiency in PHB production;
  (ix) deficiency in Slr 1994 expression;
  (x) deficiency in Slr 1829 expression; and
  (xi) deficiency in Slr 1830 expression.

Such host cells can be used, for example, to carry out the methods of the invention. In one embodiment, the recombinant cyanobacterial host cell has been genetically engineered to reduce or eliminate Slr1125 expression. In another embodiment, the cyanobacteria is selected from the group consisting of *Synechocystis, Arthrospira maxima, Synechococcus, Trichodesmium*; and *Crocosphaera*. In a further embodiment, the recombinant cyanobacterial host cell is a *Synechocystis* sp. PCC 6803 cell.

These aspects and embodiments of the invention are described in more detail below, each of which can be combined except where the context of the specification clearly indicates otherwise.

DETAILED DESCRIPTION OF THE INVENTION

Figure 1:
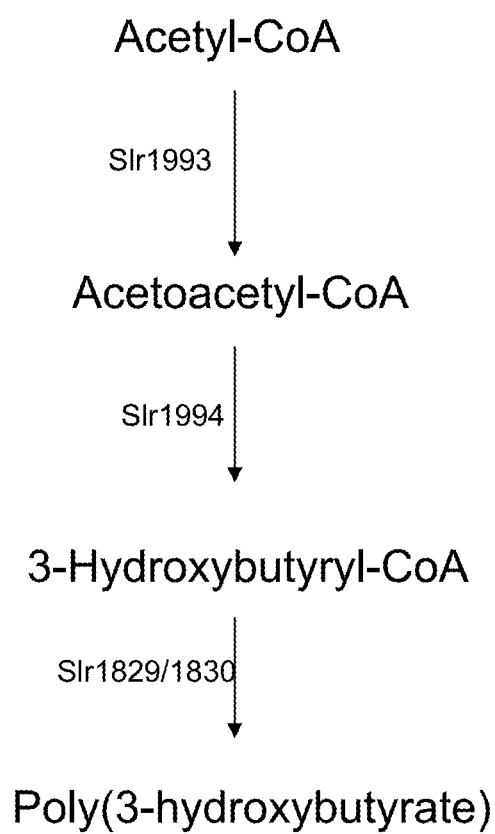
FIG. 1 is a flow chart for PHB biosynthesis in *Synechocystis*.

Within this application, unless otherwise stated, the techniques utilized may be found in any of several well-known references such as: *Molecular Cloning: A Laboratory Manual* (Sambrook, et al., 1989, Cold Spring Harbor Laboratory Press), *Gene Expression Technology* (Methods in Enzymology, Vol. 185, edited by D. Goeddel, 1991. Academic Press, San Diego, Calif.), "Guide to Protein Purification" in *Methods in Enzymology* (M. P. Deutshcer, ed., (1990) Academic Press, Inc.); *PCR Protocols: A Guide to Methods and Applications* (Innis, et al. 1990. Academic Press, San Diego, Calif.), *Culture of Animal Cells: A Manual of Basic Technique*, 2$^{nd}$ Ed. (R. I. Freshney. 1987. Liss, Inc. New York, N.Y.), and *Gene Transfer and Expression Protocols*, pp. 109-128, ed. E. J. Murray, The Humana Press Inc., Clifton, N.J.)

In one aspect, the present invention provides recombinant nucleic acids, comprising:
(a) a first nucleic acid comprising an inducible cyanobacterial promoter; and
(b) a second nucleic acid operably linked to the first nucleic acid, wherein the second nucleic acid encodes an inhibitory nucleic acid complementary to a target nucleic acid sequence that encodes an amino acid sequence of one or more polypeptides selected from the group consisting of SEQ ID NO:2, SEQ ID NO:4, SEQ ID NO:6, and SEQ ID NO:8.

The recombinant nucleic acids of this first aspect of the invention can be used, for example, as constructs for producing recombinant cyanobacteria to control Slr1125 (or orthologue thereof) production. The Slr1125 protein is a carotenoid glycosyl transferase involved in the biosynthesis of myxoxanthophyll and the recombinant nucleic acids of the invention can be used, for example, to produce bioplastics (such as polyhydroxyalkanoates ("PHA"), which include, for example, PHBs as discussed below) and cyanophycin in larger quantity in cyanobacteria than previously possible, based at least in part on the induction of cell conversion into granule formation and biopolymer production by Slr1125 down-regulation, due to interruption of the carotenoid biosynthesis/degradation pathway.

SEQ ID NO:2 is the amino acid sequence of *Synechocystis* sp. PCC 6803 Slr1125. The filamentous cyanobacterium *Trichodesmium erythraeum* IMS 101 has an Slr1125 orthologue (SEQ ID NO:8), with 55% identity at the amino acid level, while the *Crocosphaera watsonii* WH 8501 (previously known as *Synechocystis* sp. WH 8501) Slr1125 apparently has been split up into two open reading frames, recited in SEQ ID NO:4 and SEQ ID NO:6.

Thus, the recombinant nucleic acids incorporating a second nucleic acid encoding an inhibitory nucleic acid complementary to a nucleic acid sequence encoding one or more of the Slr1125 orthologues can also be used to produce bioplastics in larger quantity in cyanobacteria than previously possible.

As used herein, "recombinant nucleic acids" are those that have been removed from their normal surrounding nucleic acid sequences in the genome or in cDNA sequences. Such recombinant nucleic acid sequences may comprise additional sequences useful for promoting expression of the inhibitory nucleic acid, or any other useful signals.

The term "operably linked" refers to the association of the first and second nucleic acids in a single recombinant nucleic acid so that the expression of the second nucleic acid is activated by the first nucleic acid. Thus, the first nucleic acid is operably linked to the second nucleic acid when it is capable of affecting the expression of the second nucleic acid.

As used herein, the term "expression" refers to the transcription of sense (mRNA) or antisense RNA derived from the nucleic acid fragment of the invention. Expression may also refer to translation of mRNA into a polypeptide.

The term "inhibitory nucleic acid" means any type of nucleic acid that could inhibit expression (transcription or translation), or accumulation of the expression product (RNA or protein), of its target nucleic acid sequence. Such inhibitory nucleic acids include, but are not limited to, antisense nucleic acids, small interfering nucleic acids, ribozymes, and aptamers that bind the target nucleic acid.

"Antisense RNA" refers to a RNA transcript that is complementary to all or part of a target primary transcript or mRNA and that blocks the expression of a target gene (U.S. Pat. No. 5,107,065). The complementarity of an antisense RNA may be with any part of the specific gene transcript, i.e., at the 5' non-coding sequence, 3' non-coding sequence, introns, or the coding sequence. "Functional RNA" refers to antisense RNA, ribozyme RNA, or other RNA that is not translated yet has an effect on cellular processes. "Sense"

RNA refers to RNA transcript that includes the mRNA and so can be translated into protein by the cell.

"Antisense inhibition" refers to the production of antisense RNA transcripts capable of suppressing the expression of the target protein. "Co-suppression" refers to the production of sense RNA transcripts capable of suppressing the expression of identical or substantially similar foreign or endogenous genes (U.S. Pat. No. 5,231,020).

The term "complementary" is used to describe the relationship between nucleotide bases that are capable to hybridizing to one another. For example, with respect to DNA, adenosine is complementary to thymine and cytosine is complementary to guanine. The inhibitory nucleic acid is complementary to the target nucleic acid over a region large enough to inhibit expression or accumulation of the target nucleic acid expression product. In one embodiment, the inhibitory nucleic acid is complementary to at least 20 contiguous nucleotides of the target nucleic acid; in various further embodiments, the inhibitory nucleic acid is complementary to at least 30, 50, 100, 250, or 500 contiguous nucleotides of the target nucleic acid, or is complementary to the entire nucleic acid sequence of the target nucleic acid.

"Promoter" refers to a DNA sequence capable of controlling the expression of the second nucleic acid. In general, the second nucleic acid is located 3' to the inducible promoter, although any arrangement that permits an operable linkage of the first and second nucleic acids can be used. "Inducible" means that the promoter does not constitutively activate expression of the second nucleic acid, but allows for regulated expression. The inducible promoters may be derived in their entirety from a native gene, or be composed of different elements derived from different promoters found in nature, or even comprise synthetic DNA segments. It is understood that since in most cases the exact boundaries of regulatory sequences have not been completely defined, DNA fragments of different lengths may have identical promoter activity.

The term "Cyanobacterial promoter" means that the promoter is capable of directing expression of the second nucleic acid in a cyanobacteria (for example, *Synechocystis, Trichodesmium*, and *Crocosphaera*), and is not limited to promoters derived from cyanobacteria.

In one embodiment of this first aspect, the target nucleic acid sequence comprises or consists of a nucleic acid selected from SEQ ID NO:1, SEQ ID NO:3, SEQ ID NO:5, and SEQ ID NO:7, which are the coding DNA for SEQ ID NOS: 2, 4, 6, and 8, respectively.

As will be understood by those of skill in the art, the inhibitory nucleic acid can be used in different cyanobacterial species, so long as it has sufficient identity with the target nucleic acid sequence. In a preferred embodiment, the strain from which the inhibitory nucleic acid is derived is used. In prokaryotes, the gene is translated during its transcription, so the RNA is usually connected from one side with the transcription enzymes and the other end has the ribosome attached to it for translation. Therefore, in further embodiments, a full length antisense-RNA molecule is used so it can bind to whatever exposed segment of the RNA molecule during the transcription-translation process, in addition to full binding to the free RNA molecules. These embodiments also ensure the maximum specificity of inhibition.

The first nucleic acid comprises or consists of an inducible cyanobacterial promoter. As used herein, "inducible" means that the expression of the inhibitory nucleic acid from the promoter can be regulated and thus increased or decreased as desired by application of an appropriate stimulus to cells in which the promoter is functional, Any inducible promoter capable of replicating in cyanobacteria can be used, while those inducible in cyanobacteria selected from the group consisting of *Synechocystis, Arthrospira maxima Trichodesmium*, and *Crocosphaera* are preferred. In one embodiment, the inducible cyanobacterial promoter comprises a plastocyanin promoter (inducible by copper), according to SEQ ID NO:9, or a functional equivalent thereof. In other embodiments, the inducible cyanobacterial promoter comprises or consists of an inducible promoter as disclosed in US20040157331 or US20020164706.

The recombinant nucleic acids of this aspect of the invention can comprise further functional components as desired for a given application. For example, the constructs can comprise one or more further nucleic acids that encode expression products of interest; such further nucleic acids can be operably linked to the inducible promoter, or can be operably linked to one or more further promoters present in the recombinant nucleic acid. In one such embodiment, the recombinant nucleic acids further comprise a third nucleic acid that encodes an $NAD^+$ synthetase protein (Slr1691) that comprises or consists of the amino acid sequence of SEQ ID NO:10 (*Synechocystis*), 11 (*Crocosphaera Watsonii* WH 8501), or 12 *Trichodesmium Erythraeum* IMS101). In a further embodiment of this first aspect of the invention, the third nucleic acid comprises or consists of a NAD synthetase coding sequence according to SEQ ID NO:13 (*Synechocystis*), 14 (*Crocosphaera Watsonii* WH 8501), or 15 (*Trichodesmium Erythraeum* IMS101).

In another embodiment of this first aspect of the invention, the recombinant nucleic acids further comprise a fourth nucleic acid that encodes Sll1415, the putative NAD+-kinase, which comprises or consist of the amino acid sequence of SEQ ID NO:16 (*Synechocystis* sp. PCC 6803), 18 *Crocosphaera watsonii* WH 8501), or 20 (*Trichodesmium erythraeum* IMS101), together with slr1691. In a further embodiment, the fourth nucleic acid comprises or consists of a NAD+-kinase coding sequence according to SEQ ID NO:17 (*Synechocystis* sp. PCC 6803)), 19 *Crocosphaera watsonii* WH 8501)), or 21 (*Trichodesmium erythraeum* IMS101).

PHA biosynthesis requires NADPH as a cofactor; therefore increasing NAD biosynthesis could enhance PHA production. Thus, the present invention provides cyanobacterial recombinants in which a copy of the NAD synthetase and/or the NAD+-kinase, can be introduced in front of the inducible promoter (such as the copper-controlled promoter), to over express NAD synthetase and/or the NAD+-kinase in coordination with the induction of PHA biosynthesis, thereby increase the availability of the cofactor required for PHA biosynthesis.

The nucleic acids of the first aspect of the invention can further comprise "recombination sequences" for promoting double homologous recombination in a cyanobacterial genome. As used herein, "Double Homologous recombination" means the exchange of DNA fragments between two DNA molecules at two sites of identical nucleotide sequences. Thus, the "recombination sequences" comprise two nucleic acids that flank the regions desired to be recombined into the genome, wherein the recombination sequences are identical to sequences in the cyanobacterial genome that are targeted for insertion of the recombinant nucleic acids of the invention. See, for example, Mes and Stal, Gene. 2005 Feb. 14; 346:163-71; and Mes and Doeleman, J Bacteriol. 2006 October; 188(20):7176-85. In one embodiment, the region of the cyanobacterial genome target for insertion can be a non-protein coding region; in other embodiments, the targeted region of the cyanobacterial genome can be a protein-encoding gene to be disrupted, thus providing the ability to generate mutant cyanobacteria that cannot express the disrupted protein-encoding gene, and which also express the recombinant nucleic acids of the invention. Further examples of these embodiments are provided below.

The recombinant sequences of any of the embodiments of this first aspect can further comprise sequences to promote replication in an organism of choice. Such sequences are well known in the art. For example, commercially available vectors (plasmid or viral) can be used with such replication capabilities, and the recombinant nucleic acids of the invention can be cloned into the vector. Such replication competent vectors are useful, for example, to produce large quantities of the recombinant nucleic acids of the invention. The organism of choice can be any organism in which replication of the recombinant nucleic acids would be useful, including but not limited to E. coli.

The recombinant nucleic acids of the first aspect of the invention, and vectors comprising the recombinant nucleic acids of the first aspect of the invention, may further comprise nucleic acid sequences encoding a selectable marker to, for example, facilitate selection of host cells expressing the vector. The recombinant nucleic acids and vectors may contain other promoter sequences and other encoded nucleic acids or polypeptides, as discussed in more detail below, as well as relevant control signals (ie, leader, transcriptional and translational stop signals), and polylinkers for introducing specific restriction sites facilitating ligation in specific regions of the recombinant nucleic acids.

These embodiments of the first aspect of the invention can be combined except where the context of the specification clearly indicates otherwise.

In a second aspect, the present invention provides recombinant host cells that (a) possess chromosomally integrated recombinant nucleic acids of the first aspect of the invention; and/or (b) are transfected with replication competent vectors comprising the recombinant nucleic acids of the first aspect of the invention. Such recombinant host cells can be either prokaryotic or eukaryotic, with prokaryotic host cells preferred. For example, the recombinant host cells transfected with recombinant expression vectors constructed to permit expression in, for example, E. coli, can be used for production of large quantities of the recombinant expression vectors and the recombinant nucleic acids of the invention. Double homologous recombination is discussed above. Recombinant cyanobacterial host cells including, but not limited to, cyanobacteria selected from the group consisting of Chlorococcales (including Synechocystis and Synechococcus, with Synechocystis sp. PCC 6803 and Synechococcus MA19 being preferred), Trichodesmium; and Crocosphaera, and specific strains disclosed in the Examples below, can be used, for example, to produce large quantities of bioplastics, as discussed in more detail below. Transfection of expression vectors into prokaryotic and eukaryotic cells can be accomplished via any technique known in the art, including but not limited to standard bacterial transformations, calcium phosphate co-precipitation, electroporation, or liposome mediated-, DEAE dextran mediated-, polycationic mediated-, or viral mediated transfection. (See, for example, Molecular Cloning: A Laboratory Manual (Sambrook, et al., 1989, Cold Spring Harbor Laboratory Press; Culture of Animal Cells: A Manual of Basic Technique, 2$^{nd}$ Ed. (R. I. Freshney. 1987. Liss, Inc. New York, N.Y.). Double homologous recombination for producing recombinant cyanobacterial host cells is discussed above; see also Koksharova and Wolk, Appl Microbiol Biotechnol. 2002 February; 58(2): 123-37; and Golden, Methods Enzymol. 1988; 167:714-27.

Recombinant cyanobacteria of the second aspect of the invention produce large amounts of PHA and cyanophycin. In some cases, it may be desirable to produce large amounts of only one of these products to, for example, facilitate isolation of the product of interest. This can be accomplished by further modifying the recombinant cyanobacteria of the second aspect of the invention to produce only one of these two major products. Thus, in various further embodiments of any of the above embodiments, the recombinant cyanobacterial cells of the second aspect of the invention may further be deficient in one of:

(a) Cyanophycin expression; or
(b) poly-β-hydroxyalkanoate (PHA) expression.

Thus, in one set of further embodiments of the second aspect of the invention, a recombinant cyanobacterial host cell according to the invention is further deficient in expression of cyanophycin. In an alternative set of further embodiments of the second aspect of the invention, any of the recombinant host cells are further deficient in PHA expression. As used herein, "PHA" (also referred to herein as a "bioplastic", which is a polymer of biological origin) includes any PHA in the cyanobacteria being manipulated, including but not limited to 3-hydroxybutyryl-CoA, and poly(3-hydroxybutyrate) ("PHB").

Any mechanism for creating the recited deficiency can be used, including but not limited to gene knockouts using double homologous recombination and the construction of recombinant nucleic acids with a promoter operably linked to an inhibitory nucleic acid that is complementary to the expression product of a gene involved in cyanophycin expression (including but not limited to cyanophycin synthetase) or PHA expression (including but not limited to PHA synthetase); exemplary genes are discussed below. If inhibitory nucleic acids are used, the operably linked promoter can be a constitutive or inducible promoter; in either case the recombinant nucleic acid can be linked in a single construct with the recombinant nucleic acids of the first aspect of the invention, or can be constructed as a recombinant nucleic acid separate from the recombinant nucleic acids of the first aspect of the invention.

In one embodiment, recombinant host cells of the second aspect of the invention are deficient in cyanophycin expression; this strain is particularly useful for PHA production. In another embodiment, the cyanophycin expression deficiency results from deletion of the cyanophycin synthetase gene from Synechocystis (SEQ ID NO:22) in the cyanobacteria. Examples of these embodiments are provided below.

Alternatively, the recombinant host cell of the second aspect of the invention may further comprise an expression vector comprising a nucleic acid construct comprising a promoter sequence operatively linked to a nucleic acid encoding an inhibitory nucleic acid complementary to a target nucleic acid sequence that encodes an amino acid sequence of Synechocystis cyanophycin synthetase (SEQ ID NO:23) (Slr2002). In a further embodiment, the inhibitory nucleic acid is an antisense transcript that comprises at least 20 contiguous nucleotides of the nucleic acid sequence of SEQ ID NO:22 (slr2002). In various further embodiments, the antisense transcript comprises at least a contiguous 30, 50, 100, 250, 500, or the entire nucleic acid sequence of SEQ ID NO:22. In a preferred embodiment, the nucleic acid encoding the antisense transcript is operably linked to the cyanobacterial inducible promoter.

In an alternative embodiment, the recombinant cyanobacterial cells of the second aspect of the invention are deficient in PHA expression, wherein the PHA expression deficiency results from deletion of the slr1993 gene (SEQ ID NO:24; from *Synechocystis*). This embodiment is particularly useful for cyanophycin production. An example of this embodiment is provided below. Alternatively, the recombinant host cell may further comprise an expression vector comprising a nucleic acid construct comprising a promoter sequence operatively linked to a nucleic acid encoding an inhibitory nucleic acid complementary to a target nucleic acid sequence that encodes the amino acid sequence of SEQ ID NO:25 (Slr1993). In a further embodiment, the inhibitory nucleic acid is an antisense transcript that comprises at least 20 contiguous nucleotides of the nucleic acid sequence of SEQ ID NO:24. In various further embodiments, the antisense transcript comprises at least a contiguous 30, 50, 100, 250, 500, or the entire nucleic acid sequence of SEQ ID NO:24. In a preferred embodiment, the nucleic acid encoding the antisense transcript is operably linked to a cyanobacterial inducible promoter, such as the plastocyanin promoter discussed above.

Host cells combining the slr1125 mutant and the PHA deficient mutants can be used, for example, for production/isolation of cyanophycin, since PHA will not be abundantly expressed. In a further embodiment, these host cells may further include a second inhibitory nucleic acid whose expression is under control of the inducible promoter, wherein the second inhibitory nucleic acid is complementary to a target nucleic acid that encodes cyanophycinase (Slr2001; see SEQ ID NO:26 from *Synechocystis*), which degrades cyanophycin granules. In this embodiment, it is preferred that the second inhibitory nucleic acid targeting cyanophycinase and the inhibitory nucleic acid targeting slr1125 are both under control of the same inducible promoter. The second inhibitory nucleic acid may be an antisense transcript that comprises at least 20 contiguous nucleotides of the nucleic acid sequence of SEQ ID NO:27. In various further embodiments, the antisense transcript comprises at least a contiguous 30, 50, 100, 250, 500, or the entire nucleic acid sequence of SEQ ID NO:27. In an alternative embodiment, the cyanophycinase deficiency results from deletion of the slr2001 gene (SEQ ID NO:27), or orthologue thereof.

PHB Pathway in *Synechocystis*.

Polyhydroxybutyrates (PHB), are intracellular reserve materials produced by a large number of bacteria including cyanobacteria. In *Synechocystis*, three enzymes are involved in the conversion of acetyl-CoA to PHB: beta ketothiolase (Slr1993), acetoacetyl-CoA reductase (Slr1994) and PHB polymerase (Slr1829 and Slr1830; these two ORFs encode two polypeptides which form the PHB heterodimer; absence of one or both is sufficient to completely eliminate PHB polymerase activity). Two acetyl-CoA groups are condensed by beta-ketothiolase to form acetoacetyl-CoA. The acetoacetyl-CoA is then reduced by an NADP-specific reductase to form D(−)-beta-hydroxybutyryl-CoA, the substrate for PHB polymerase.

In further embodiments, the recombinant cyanobacteria of the second aspect of the invention can be rendered deficient for expression of other PHA (such as PHB) biosynthesis pathway gene(s), resulting in a desired PHA pathway end product. These embodiments can preferably be combined with embodiments in which cyanophycin expression is inhibited, thus resulting in recombinant cyanobacteria that produce a desired PHA. A flow chart for PHB biosynthesis in *Synechocystis* is provided in FIG. 1.

Thus, in various further embodiments, the recombinant cyanobacteria of the second aspect of the invention are further rendered deficient in expression of one or more of:
 Slr1994 (SEQ ID NO:28);
 Slr1829 (SEQ ID NO:29); and
 Slr1830 (SEQ ID NO:30). (Taroncher-Oldenburg et al., Appl Environ Microbiol. 2000 October; 66(10):4440-8; Hein et al., Arch Microbiol. 1998 September; 170(3):162-70)

Those cells rendered deficient in slr1994 expression can be used, for example, to produce acetoacetyl-CoA, which is useful, in one example, for feed stock for other bacteria to produce other desired chemicals; those rendered deficient in one or both of slr1829 and slr1830 can be used, for example, to produce poly(3-hydroxybutyryl-CoA), which can be used to produce 3-hydroxybutyryl-CoA and or 3-hydroxybutyryl monomer which is valuable as feed stock for other bacteria or for direct use as a biofuel.

In one embodiment, the expression deficiency results from deletion of the relevant gene (SEQ ID NO:31, 32, and/or 33) in the cyanobacteria. Examples of this embodiment are provided below. Alternatively, the recombinant cyanobacteria of the second aspect of the invention may further comprise an expression vector comprising a nucleic acid construct comprising a promoter sequence operatively linked to a nucleic acid encoding an inhibitory nucleic acid complementary to a target nucleic acid sequence that encodes an amino acid sequence of one or more of SEQ ID NO:28, SEQ ID NO:29, and SEQ ID NO:30. In a further embodiment, the inhibitory nucleic acid is an antisense transcript that comprises at least 20 contiguous nucleotides of the nucleic acid sequence of one or more of SEQ ID NO:31, SEQ ID NO:32, and SEQ ID NO:33. In various further embodiments, the antisense transcript comprises at least a contiguous 30, 50, 100, 250, 500, or the entire nucleic acid sequence of SEQ ID NO:31, SEQ ID NO:32, and SEQ ID NO:33. In a preferred embodiment, the nucleic acid encoding the antisense transcript is operably linked to a cyanobacterial inducible promoter, such as the plastocyanin promoter discussed above.

In an alternative embodiment, the recombinant cyanobacterial cells of the second aspect of the invention are deficient in PHA expression, wherein the PHA expression deficiency results from deletion of the slr1993 gene (SEQ ID NO:24), or orthologue thereof. An example of this embodiment is provided below. Alternatively, the recombinant host cell may further comprise an expression vector comprising a nucleic acid construct comprising a promoter sequence operatively linked to a nucleic acid encoding an inhibitory nucleic acid complementary to a target nucleic acid sequence that encodes the amino acid sequence of SEQ ID NO:25. In a further embodiment, the inhibitory nucleic acid is an antisense transcript that comprises at least 20 contiguous nucleotides of the nucleic acid sequence of SEQ ID NO:24. In various further embodiments, the antisense transcript comprises at least a contiguous 30, 50, 100, 250, 500, or the entire nucleic acid sequence of SEQ ID NO:24. In a preferred embodiment, the nucleic acid encoding the antisense transcript is operably linked to a cyanobacterial inducible promoter, such as the plastocyanin promoter discussed above.

The following are specific examples of recombinant nucleic acid constructs that fall within the scope of the present invention, together with specific uses for such constructs.

Figure 2:
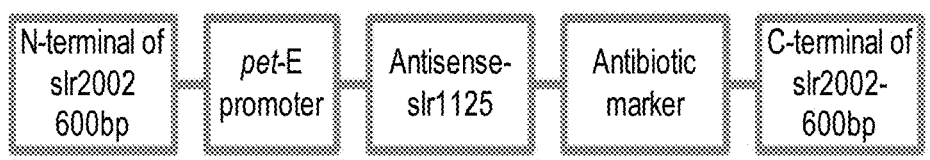
FIG. 2 is a schematic diagram of an exemplary recombinant nucleic acid construct that can be used, for example, to create a stable transfected cyanobacterial strain for PHA production.

FIG. 2 provides a schematic diagram of an exemplary construct that can be used, for example, to create a stable transfected cyanobacterial strain for PHA production. The construct can be cloned into any standard vector for purposes of propagation in, for example, E. coli. Any antibiotic resistance marker suitable for use with the host cells of the invention can be used, including but not limited to chloramphenicol.

Each box represents a segment of DNA. The "N-terminal" and "C-terminal" of slr2002 is an abbreviation for the upstream and downstream sites for double homologous recombination with the genomic slr2002 gene. Slr2002 is the cyanophycin synthetase gene discussed above (SEQ ID NO:22). As will be understood by those of skill in the art, the use of 600 bp of the 5' sequence of slr2002 (SEQ ID NO:34) or 3' sequence of slr2002 (SEQ ID NO:35) is exemplary. In various embodiments, 200 or more nucleotides can be used, with a larger number of nucleotides preferred.

Inserting the nucleic acid construct comprising a nucleic acid encoding an antisense-slr1125 operably linked to the copper-controlled petE promoter inside the slr2002 homologous recombination sequences and transfecting a cyanobacterium with the construct via double homologous recombination results in recombinant cyanobacteria that produce large amounts of PHA in the presence of copper, but are unable to synthesize cyanophycin granules, thus facilitating exclusive production and purification of PHA from the host cells without interference from cyanophycin.

Figure 3:
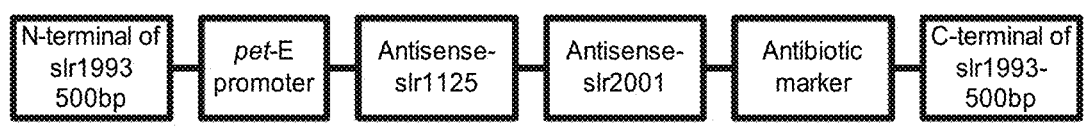
FIG. 3 is a schematic diagram of a recombinant nucleic acid that is effective for creating a stable cyanophycin-producing cyanobacterial strain.

FIG. 3 provides a schematic of a recombinant nucleic acid according to the invention that is effective for creating a stable cyanophycin-producing strain for pure cyanophycin production. In this case, the recombination sequences are derived from slr1993 (PHA-specific beta-ketothiolase gene) (SEQ ID NO:24), so a recombinant cyanobacterium transfected with this construct via double homologous recombination is deleted for this gene and does not synthesize PHA. The construct further comprises nucleic acids encoding antisense-slr1125 and also antisense slr2001, the gene for cyanophycinase, which degrades cyanophycin granules (see above), each operably linked to the copper-controlled petE promoter.

Thus, exposure of the cells to copper will result in antisense expression from the construct, which will down regulate cyanophycinase, while antisense-slr1125 will induce the cyanophycin granule formation in the absence of PHB biosynthesis and cyanophycin degradation.

Figure 4:
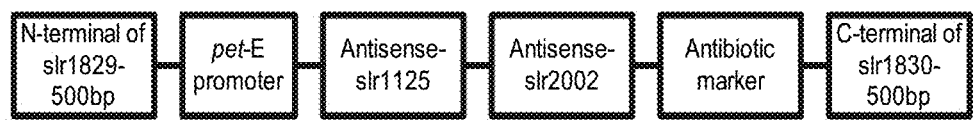
FIG. 4 is a schematic diagram of a recombinant nucleic acid suitable for production of 3-hydroxybutyrate.

FIG. 4 shows a schematic diagram of a recombinant nucleic acid of the invention suitable for production of 3-hydroxybutyrate. In this case, the recombination sequences are derived from slr1829 (poly(3-hydroxyalkanoate synthase gene) (SEQ ID NO:32)), so a recombinant cyanobacterium transfected with this construct via double homologous recombination is deleted for this gene and does not synthesize PHB.

The construct further comprises nucleic acids encoding antisense-slr1125 and also antisense slr2002, the gene for cyanophycin synthetase (SEQ ID NO: 22), each operably linked to the copper-controlled petE promoter. Thus, exposure of the cells to copper will result in antisense expression from the construct, which will down regulate cyanophycin expression, while antisense-slr1125 will induce the accumulation of 3-hydroxybutyryl acid as a monomer without polymerization due to the absence of a functional slr1829 gene.

These embodiments of the second aspect of the invention can be combined as desired, as well as combined with various embodiments of the first aspect of the invention except where the context of the specification clearly indicates otherwise.

In a third aspect, the present invention provides methods for producing biomaterials, comprising:
(a) culturing cyanobacterial host cells that are deficient in Slr1125 expression;
(b) harvesting the cyanobacterial host cells; and
(c) preparing biomaterials from the harvested cyanobacterial host cells.

The methods of the invention can be used, for example, to produce quantities of biomaterials not previously possible using known cyanobacterial host cells. The cyanobacterial host cells may be naturally deficient in Slr1125 expression, or may be genetically engineered to reduce or eliminate Slr1125 expression. In one embodiment, such engineering comprises deleting the slr1125 gene. In another embodiment, such engineering comprises use of host cells as disclosed above, in which slr1125 is under control of an inducible promoter, such that expression of Slr1125 can be controlled as desired. For example, antisense technology can be achieved using the native copper-controlled plastocyanin promoter with slr1125 in the antisense direction behind it, as discussed above, permitting down-regulating the expression of Slr1125 by adding μM amounts of copper to the medium. This protocol provides a direct and cheap way of controlling slr1125 gene expression.

The inventors have discovered that cyanobacteria deficient in Slr1125 expression are capable of producing large amounts of granules and releasing their granules content, in which a mixture of PHA and cyanophycin are the predominant products, facilitating production of much large amounts of these products than was possible in the art.

All of the embodiments of the recombinant nucleic acids and host cells of the first and second aspects of the invention are equally applicable for use in this third aspect of the invention. As disclosed above, the various embodiments were all based on combinations with the inducible slr1125 inhibitor construct; in this third aspect, all of the various embodiments above are equally compatible, alone or in combination, for use with the slr1125 deletion mutant.

Thus, in one exemplary embodiment, the biomaterials produced comprise biomaterials selected from the group consisting of polyhydroxyalkanoates (PHA) and cyanophycin. In another embodiment, the cyanobacterial host cells are selected from the group consisting of Synechocystis, Arthrospira maxima, Synechococcus, Trichodesmium, and Crocosphaera. In a further embodiment, the cyanobacterial host cells are Synechocystis PCC 6803 cells. In another embodiment, the cyanobacterial host cells have been genetically engineered to overexpress NAD synthetase and/or NAD+ kinase, wherein the culturing comprises culturing the recombinant cyanobacterial host cells under conditions suitable to overexpress NAD synthetase and/or NAD+ kinase.

In a further embodiment, the method comprises preparation of PHA, wherein the cyanobacterial host cells are deficient in cyanophycin production, for example, by recombinantly engineering the cyanobacterial host cells to reduce or eliminate expression of cyanophycin synthetase in the cyanobacterial host cells. In another embodiment, the method comprises preparation of cyanophycin, wherein the cyanobacterial host cells are deficient in PHA production, for example, by recombinantly engineering the cyanobacterial host cells to reduce or eliminate expression of Slr1993 in the cyanobacterial host cells. In another embodiment, the cyanobacterial host cells are deficient in cyanophycinase expression.

In another embodiment, the method comprises preparation of PHA, wherein the cyanobacterial host cells are deficient in production of polyhydroxybutyrates (PHB), for example, by recombinantly engineering the cyanobacterial host cells to reduce or eliminate expression of one or more of Slr1994, Slr1829, and Slr1830. In one embodiment, the cyanobacterial host cells have been genetically engineered to reduce or eliminate expression of Slr1994, and wherein the method comprises production of acetoacetyl-CoA. In another embodiment, the cyanobacterial host cells have been genetically engineered to reduce or eliminate expression of one or both of Slr1829 and Slr1830, and wherein the method comprises production of poly(3-hydroxybutyryl-CoA).

Preparation of nucleic acid constructs and recombinant cyanobacterial host cells according to these various embodiments are described in detail above.

The culture conditions used can be any that are suitable for production of the biomaterials of interest. Exemplary culture conditions for slr1125 deletion mutants are provided in the examples below. A major advantage in using cyanobacteria for bioplastics production is that solar energy provides the energy input. In one example, cyanobacteria can be grown at between 25° C. and 34° C. (for example, *Synechocystis* sp. PCC 6803 grows between 25° C.-34° C. with optimum temperature (30° C.)), with shaking in a media such as buffered BG-11 medium (40) in the presence of appropriate light conditions, such as between 50 to 200 µmol of photons $m^{-2} s^{-1}$, where 50 is low light and 200 is high light. As will be understood by those of skill in the art, large scale production cells can be adapted to different light regimes according to location and the bioreactor specifications, for example, up to 600 µmol of photons $m^{-2} s^{-1}$ which is approximately equivalent to a bright sunny day by taking into account the self shading effect of the cells. Light conditions can vary as appropriate for a given purpose, and can be continuous or periodic; for large scale and outdoor cultivation, light/dark cycling is preferred to minimize the cost and avoid extra cost from artificial lighting. Under such conditions, large scale cyanobacterial growth can result in high density cultures.

In one embodiment, granulation is induced during cell growth by substituting ammonia for nitrates as the nitrogen source in the growth medium. Cyanobacteria do not fix nitrogen and thus a nitrogen source is needed in the growth medium; using ammonia as the nitrogen source eliminates the need for cyanobacterial conversion of nitrates to ammonia, limits consumption of NADPH reducing power, and permitting increased NADPH reserves in the cells for granulation and biomaterials biosynthesis during the induction phase. In one embodiment, the amount of ammonia is approximately equimolar to the amount of nitrates in the standard growth medium; in another embodiment, the amount of ammonia ranges from 0.75 g/L to 1.5 g/L; in another embodiment, it ranges from 0.75 g/L to 1.25 g/L; in another embodiment, it ranges from 0.75 g/L to 1.0 g/L. In a further embodiment of any of these granulation embodiments, cells can be grown to maximal density, and granulation induced to maximize production of biomaterials of interest, such as PHB, cyanophycin and 3-hydroxybutyrate. In a further embodiment, the cyanobacterial cells have been recombinantly engineered to inducibly down-regulate expression of the slr1125 gene, such as by inclusion of a copper-inducible promoter, as disclosed above. In a further embodiment, NAD synthetase and/or NAD kinase can be overexpressed in conjunction with sh-1125 down-regulation or deletion. In one non-limiting example, *Synechocystis* sp. PCC 6803 has a doubling time of 8-10 hours. Therefore, biomass of 4-5 $OD_{730}$/Liter can be divided into two halves: one can be further grown to allow a continuous supply of cell-biomass, while the other half can be used to stimulate granule production as discussed above.

In a further embodiment, granulation can be induced by including an inhibitor of lycopene cyclase in the growth medium; examples of such inhibitors include, but are not limited to, nicotinic acid (5-50 uM), chlorophenoxytriethylamine (COPTA), 2-(4-chlorophenylthio)-triethylamine (CAPT), 2-(3,4-dichlorophen-oxy)-triethylamine (DCPTA), 2-(3,5-dimethylphenoxy)-triethylamine (DMPTA), 2-(4-methyl-phenoxy)-triethylamine (MPTA), aminotriazole, azasqualene, dodecyltrimethylammonium, N,N-dimethyl-dodecylamine, imidazole, piperonyl butoxide, piperidine, triethylamine, and pyridine. The use of such inhibitors enhances granule formation and reduces granulation time after the cell culture reaches its maximum density. In one embodiment, the culture media includes nitrates as a nitrogen source; in another embodiment, ammonia is provided as a nitrogen source. Any of the slr1125 constructs can be used with the deletion mutant being preferred for embodiments employing carotenoid biosynthesis inhibitors (e.g. desaturases and cyclases).

Carotenoid is a group of $C_{40}$ hydrocarbons that is synthesized from polymerization of Isopentenyl pyrophosphate (IPP) with its isomer, dimethylallyl pyrophosphate (DMPP), both are $C_5$ hydrocarbon molecules, through a sequential steps until it form phytoene ($C_{40}$ molecules). This molecule is the first committed carotenoid molecule synthesized in the carotenoid biosynthesis pathway of the *cyanobacterium Synechocystis* sp. PCC 6803. Introduction of four double bounds to the phytoene molecule produces a desaturated $C_{40}$ lycopene by the action of two carotene desaturases enzymes (phytoene desaturase and zeta-carotene desaturase). Lycopene is further cyclized by lycopene cyclase to produce monocyclic (Gamma-carotenel) or dicyclic carotenes (Beta-carotene). In the case of myxoxanthophyll additional enzymes are required to further modify monocyclic carotenoid molecules to produce the glycosylated molecule (sll0254, slr1293 and slr1125), the product of these genes are major enzymes required for the final formation of myxoxanthophyll carotenoid glycoside. The final major carotenoids are further processed to smaller carotenoid products (e.g. retinal group). The inhibitors listed below inhibit one or more of the carotenoid biosynthesis/degradation enzymes and block the biosynthesis of myxoxanthophyll. Therefore, using one or more of these inhibitors with combinations of the host cells of the invention provides additional control to produce and increase biomaterials (such as PHB and cyanophycin) and reduces the granulation time needed for full conversion of cell to granules. In one embodiment, one or more of the inhibitor are used for large scale production of PHB and cyanophycin from cyanobacteria to further improve both quantity and the quality of the final product and minimize the cost. Table 1 provides preferred concentration ranges in culture media for the inhibitors.

TABLE 1

| Inhibitors | Preferred concentration range |
| --- | --- |
| 1-COPTA, chlorophenoxytriethylamine, | 5 ug/L-25 ugl/L |
| 2-CAPT (2-(4-chlorophenylthio)-triethylamine); | 5 ug/L-25 ugl/L |
| 3-DCPTA, 2-(3,4-dichlorophen-oxy)-triethylamine | 25 ug/L-50 ugl/L |
| 4-DMPTA, 2-(3,5-dimethylphenoxy)-triethylamine | 25 ug/L-50 ugl/L |
| 5-MPTA, 2-(4-methyl-phenoxy)-triethylamine | 15 ug/L-50 ugl/L |
| 6-Aminotriazole | 0.5 mg/L-1.5 mgl/L |
| 7-Azasqualene | 5 ug/L-15 ugl/L |
| 8-Azasqualene | 50 ug/L-250 ugl/L |

TABLE 1-continued

| Inhibitors | Preferred concentration range |
|---|---|
| 9-Dodecyltrimethylammonium | 2 ug/L-25 ugl/L |
| 10-N,N-Dimethyldodecylamine | 25 ug/L-250 ugl/L |
| 11-imidazole | 250 ug/L-500 ugl/L |
| 12-piperonyl butoxide | 5 ug/L-50 ugl/L |
| 13-piperidine | 50 ug/L-100 ugl/L |
| 14-triethylamine | 50 ug/L-150 ugl/L |
| 15-pyridine | 100 ug/L-150 ugl/L |

The dramatic change in availability of electrons induced by the various conditions disclosed above, accumulation of NADPH, and change in light due to self shading effects greatly promote increased granule formation in the cyanobacterial host cells of the invention.

Similar culture conditions can be used for recombinant cyanobacteria that carry an inducible promoter linked to an inhibitory nucleic acid whose expression down-regulates expression of the open reading frame of slr1125 (or orthologues thereof), except that appropriate conditions for induction are used when appropriate. The relevant conditions under which to reduce slr1125 expression will be dependent on the inducible promoter used, as well as other factors, including but not limited to the specific cyanobacteria used, cyanobacterial concentration, media, pH, temperature, light exposure, etc. However, those of skill in the art can determine the specific conditions to be used, in light of the teachings herein. In one exemplary embodiment, the inducible promoter comprises the petE promoter (SEQ ID NO:9), and expression of the inhibitory nucleic acid is induced by the addition of μM amounts of copper to the media. (See, for example, (Briggs, et al., 1990)) While those of skill in the art can determine an optimal concentration of copper, ranges between 2 and 10 μM have been used under laboratory conditions. In one embodiment, an antisense slr1125 construct is downstream, and under the control of, the petE promoter. Thus, adding μM amounts of copper to the medium will result in down-regulation of slr1125 expression, granule production, and the ability to harvest the cells and prepare PHA and cyanophycin from the cells.

Harvesting of the cyanobacterial cells can be accomplished by any technique known to those of skill in the art, including but not limited to centrifugation and filtration.

Similarly, methods for preparing biomaterials from the harvested recombinant cyanobacteria can be carried out by any means known in the art, such as those described in the examples below. In one non-limiting embodiment, PHA polyesters can be recovered and purified in a procedure consisting of acidic non-PHA cell mass dissolution, pH adjustment (pH 10), and final decolorization in a bleaching solution. The major product produced by the recombinant cyanobacteria of the invention is a mixture of PHA and cyanophycin. As noted above, in various embodiments, separate cyanobacterial strains (cyanohphycin-deficient and PHA synthetase-deficient) are produced to discriminate between the biosynthesis of these two polymers.

Cyanophycin, a copolymer of L-aspartic acid and L-arginine, is produced via non-ribosomal polypeptide biosynthesis by the enzyme cyanophycin synthetase. In a further embodiment, the isolated biomaterial comprises cyanophycin, which is then partially hydrolyzed using any suitable method, including but not limited to boiling at high pH, to produce polyaspartate, which is a biodegradable substitute for chemically synthesized polycarboxylate. The latter is an anionic polyelectrolyte, which can be used as a highly effective pigment dispersing agent for use in waterborne industrial, protective coatings, gloss dispersion paints as well as printing inks. It is also used in pigment concentrates used for tinting paints, leather finishes, textiles, plastics, inks, etc. It is used in conjunction with a wide variety of binders such as physically drying acrylic dispersions, air-drying alkyd emulsions, polyester-melamine, 2-pack epoxies, acrylates etc. Therefore, this embodiment of the invention provides a very cost-effective way for cyanophycin (polyaspartate) production to replace toxic-polycarboxylates, and which can also be used as energy and water savers (ie: forming a thin film on water surface of lakes and pools to prevent water evaporation).

Thus, in various embodiments noted above, the recombinant cyanobacteria for use in the third aspect of the invention may further be deficient in cyanophycin expression or PHA expression, as disclosed above. Separation and purification of PHA polymers from non-PHA cell mass presents a technical challenge due to the solid phase of both PHA granules and non-PHA cell mass. The purity, yield, and molecular size are three major factors in PHA recovery. PHA polyesters (such as PHB) can be recovered and purified in a procedure consisting of acidic non-PHA cell mass dissolution, pH adjustment (pH 10), and final decolorization in a bleaching solution. Thus, using cells that are deficient in cyanophycin expression facilitates separation and purification of PHA produced by the recombinant cyanobacteria of the invention. Similarly, using cells that are deficient in PHA synthetase expression facilitates separation and purification of the cyanophycin produced by the recombinant cyanobacteria of the invention. PHA biosynthesis requires NADPH as a cofactor; therefore increasing NAD biosynthesis could enhance PHA production and reduce the time for full conversion to granules. Thus, as discussed above, the present invention provides cyanobacterial recombinants in which a copy of the NAD(+) synthetase can be introduced in front of the copper-controlled promoter to over express in coordination with the induction of PHA biosynthesis, thereby increasing the availability of the cofactor required for PHA biosynthesis.

In one non-limiting example, Synechocystis sp. PCC 6803 has a doubling time of 8-10 hours. Therefore, biomass of 4 $OD_{730}$/Liter can be divided into two halves: one can be further grown to allow a continuous supply of cell-biomass, while the other half can be used to granule production phase. The continuous supply of the biomass of 4-5 $OD_{730}$/Liter of cells can be achieved daily using sun light. For example: A plastic bag of 20 cm×100 cm×250 cm (width×length× height) provides a 500 L which yield approximately 1.5 kg/bag/day biomass that converted to 0.75-1.0 kg/bag/day PHA (50%) wt/wt dry biomass. The methods of the invention achieve very high and pure yield that is approximately 80-90% wt/wt dry biomass that provides 1.2-1.35 kg/bag/day PHA, which represents an unprecedented yield for these biomaterials from biologically photoautotrophic organisms to date.

In a fourth aspect, the present invention provides recombinant cyanobacterial host cells, comprising:
(a) a deficiency in Slr1125 expression; and
(b) one or more of the following recombinantly generated phenotypes:
   (i) a deficiency in cyanophycin production;
   (ii) a deficiency in poly-β-hydroxyalkanoate (PHA) production;
   (iii) overexpression of NAD synthetase;
   (iv) overexpression of NAD+ kinase;
   (v) deficiency in cyanophycin synthetase expression;

(vi) deficiency in Slr1993 expression;
(vii) deficiency in cyanophycinase expression;
(viii) deficiency in PHB production;
(ix) deficiency in Slr 1994 expression;
(x) deficiency in Slr 1829 expression; and
(xi) deficiency in Slr 1830 expression.

The host cells of this aspect of the invention can be used, for example, to prepare large amounts of biomaterials according to the methods of the invention disclosed above.

Embodiments for generating recombinant cyanobacteria) host cells with any of the recited expression deficiencies or overexpression are disclosed above and are equally applicable for use in this fourth aspect of the invention. In this aspect, the recombinant cyanobacteria) host cell has a deficiency in Slr1125 expression and at least one further altered phenotype from the recited list, which increases the capacity of the recombinant to produce biomaterials, such as PHAs and cyanophycin. In one embodiment, the deficiency in Slr1125 expression may be based on a naturally occurring deficiency. In another embodiment, the host cell is engineered to cause the deficiency, such as by deletion of the slr1125 gene. In another embodiment, such engineering comprises use of host cells as disclosed above, in which slr1125 is under control of an inducible promoter, such that expression of Slr1125 can be controlled as desired, and as disclosed in detail above.

The at least one further recombinant alteration in expression in the cyanobacterial host comprises one or more of the recited alterations, each of which is disclosed in detail above. In various further embodiments, the cyanobacteria is selected from the group consisting of *Synechocystis*, *Arthrospira maxima*, *Synechococcus*, *Trichodesmium*; and *Crocosphaera*; in a further embodiment, the recombinant cyanobacteria) host cell is a *Synechocystis* PCC 6803 cell.

EXAMPLES

Cloning of Slr1125 and Construction of the pΔslr1125S Plasmid—

The *Synechocystis* sp. PCC 6803 slr1125 gene and its flanking regions were cloned by polymerase chain reaction (PCR) based on the available *Synechocystis* genomic sequence (CyanoBase; web site: kazusa.or.jp/cyano/cyano.html) (Kaneko et al.). The forward primer was 5' CTA-GAAACGGGAATTCAAGCGGAAT 3' (SEQ ID NO: 39) with an engineered EcoR I site (underlined) and corresponding to base number 85721-85745 in CyanoBase; the reverse primer was 5' GTTTAATAGCATGCTTTGCCAGC 3' (SEQ ID NO: 40) with an engineered Sph I restriction site (underlined) and a sequence corresponding to CyanoBase bases 87845-87867 (base changes to introduce restriction sites have been bolded). The PCR-amplified sequence corresponds to slr1125 with approximately 430-450 bp flanking sequence on both sides of the ORF. A PCR product of the expected size (2.147 kb) was purified, restricted with EcoR I and Sph I (using the introduced restriction sites in the primers) and cloned into pUC 19 creating pslr1125 construct. The slr1125 gene was deleted by restriction at internal Sty I sites near the beginning and end of the slr1125 open reading frame and replacing the Sty I fragment (1.2 kb) by a 1.5 kb streptomycin resistance cassette. This creates the pΔslr1125S construct, which was used for transformation of *Synechocystis* sp. PCC 6803, carried out according to Vermaas et al. 1987. Transformants were propagated on BG-11/ agar plates supplemented with 5 mM glucose and increasing concentrations of up to 300 ug/ml of streptomycin dissolved in sterile water. The segregation state of the transformants was monitored by PCR of transformant DNA using primers recognizing sequences upstream and downstream of the slr1125-coding region. *Synechocystis* sp. PCC 6803 genomic DNA used for PCR analysis of mutants was prepared as described in He et al. The sequence of the cloned slr1125 ORF with flanking regions up and down stream was verified (SEQ ID NO:41).

Growth Conditions.

*Synechocystis* sp. strain PCC 6803 was cultivated on a rotary shaker at 30° C. in BG-11 medium (40), buffered with 5 mM N-tris (hydroxymethyl) methyl-2-aminoethane sulfonic acid-NaOH (pH 8.2). For growth on plates, 1.5% (wt/vol) Difco agar and 0.3% (wt/vol) sodium thiosulfate were added. Flux densities of 40, and 100 µmol of photons $m^{-2} s^{-1}$ from cool-white fluorescent tubes were used for growth in continuous light in liquid medium. The normal BG11 media described by Rippka et al. 1979 contains nitrate as a source of nitrogen for the growth of *Synechocystis* strains; this medium composition provides cell propagation to its maximum limit (3-5 $OD_{730}$).

Granulation Conditions.

To start the granule induction phase, the cells were diluted to 0.75 OD730 with BG11 medium containing an equimolar amount of ammonia (1 g/L) as a nitrogen source instead of nitrate; this strategy saves approximately 40% of the reducing power of NADPH, which promotes increased granule biosynthesis. Cells were cultures for an additional 48 hours under the same culture conditions discussed above. Under these culture conditions, little further cell growth occurred, as the growth conditions favored large scale granule production.

Extraction of PHB

One of the benefits of the current invention is that once granulation is induced, PHB granules float on the media surface and can be collected directly from the surface in the large scale. A one liter culture of 0.75 $OD_{730}$ cells was collected by centrifugation to collect everything in the media and precisely analyze the amount of PHB. The collected granules and cell materials were suspended in methanol (4° C., overnight) for the removal of pigments. The pellet obtained after centrifugation was dried at 60° C. and PHB was extracted in hot chloroform followed by precipitation with cold diethyl ether. The precipitate was centrifuged at 11 000 g for 20 min, washed with acetone and dissolved again in hot chloroform.

Spectrophotometric Measurement of PHB.

The spectrophotometric assay was performed as per Law and Slepecky (1961). The sample containing the polymer in chloroform was transferred to a clean test tube. The chloroform was evaporated and 10 ml of concentrated $H_2SO_4$ was added. The solution was heated in a water bath for 20 min. After cooling and thorough mixing the absorbance of the solution was measured at 235 nm against $H_2SO_4$ blank. To further confirm the presence of PHB, absorption spectra (200-1000 nm) of the sample as well as the standard (dl-β-hydroxybutyric acid, Sigma Chemical Co., USA) were compared by Spectrophotometer following acid digestion. These spectra were further compared with the spectrum of crotonic acid which is the byproduct of acid hydrolysis of PHB and the compound that absorb at 235 nm in case of standard PHB or the PHB from the cell. A total of 200 mg was collected from a 0.75 $OD_{730}$ culture flask of the slr1125 deletion strain. The absorption at 235 nm of the extracted granules was compared to standard curve generated by β-hydroxybutyric acid, Sigma Chemical Co., USA. 105 mg PHB was measured out of 200 mg cell materials which approximately give 52% PHB/Dry weight of material collected.

REFERENCES

Briggs L M, Pecoraro V L, McIntosh L. 1990. Copper-induced expression, cloning, and regulatory studies of the plastocyanin gene from the cyanobacterium *Synechocystis* sp. PCC 6803. Plant Mol. Biol. 15:633-642.

Danner R L, Joiner K A, Rubin M, Patterson W H, Johnson N, Ayers K M and Parrillo J E. 1989. Purification, toxicity, and antiendotoxin activity of polymyxin B nonapeptide. Antimicrob Agents Chemother. 1989 September; 33(9): 1428-1434

Duhring U, Axmann I M, Hess W R, Wilde A. 2006. An internal antisense RNA regulates expression of the photosynthesis gene isiA. PNAS, USA. 103:7054-7058.

He, Q., Brune, D., Nieman, R., and Vermaas, W. (1998) *Eur J. Biochem.* 253, 161-172.

Kaneko, T., Sato, S., Kotani, H., Tanaka, A., Asamizu, E., Nakamura, Y., Miyajima, N., Hirosawa, M., Sugiura, M., Sasamoto, S., Kimura, T., Hosouchi, T., Matsuno, A., Muraki, A., Nakazaki, N., Naruo, K., Okumura, S., Shimpo, S., Takeuchi, C., Wada, T., Watanabe, A., Yamada, M., Yasuda, M., and Tabata, S. (1996) DNA Res. 3, 109-136.

J. H. Law and R. A. Slepecky, Assay of poly-β-hydroxybutyric acid, J. Bacteriol. 82 (1961), pp. 33-36.

Mohamed, H. E. van de Meene A M L. Roberson R W and Vermaas W. 2005. Myxoxanthophyll is required for normal cell wall structure and thylakoid organization in the cyanobacterium *Synechocystis* sp. strain PCC 6803 . . . *J. Bacteriol.* 187:6883-6892.

Mohamed, H. E. and Vermaas W. 2006. Sll0254 ($CrtL^{diox}$) is a bifunctional lycopene cyclase/dioxygenase in cyanobacteria producing myxoxanthophyll. *J. Bacteriol.* 188: 3337-3344.

Mohamed, H. E. and Vermaas W. 2004. Slr1293 in *Synechocystis* sp. PCC 6803 is a C-3', 4' desaturase (CrtD) involved in myxoxanthophyll biosynthesis. *J. Bacteriol.* 186: 5621-5628.

Rippka, R., J. Deruelles, J. B. Waterbury, M. Herdman, and R. Y. Stanier. 1979. Generic assignments, strain histories and properties of pure cultures of cyanobacteria. J. Gen. Microbiol. 111:1-61.

Sara M, Pum D, Schuster B, Sleytr U B. 2005. S-layers as patterning elements for application in nanobiotechnology. J. Nanosci. Nanotechnol. 5:1939-1953.

Vermaas, W. F. J., Williams, G. K., and Arntzen, C. J. (1987) *Plant Mol. Biol.* 8, 317-326

Yu J, Chen L X. 2006. Cost-effective recovery and purification of polyhydroxyalkanoates by selective dissolution of cell mass. Biotechnol Prog. 22:547-553.

We claim:

1. A recombinant cyanobacterial host cell, comprising:
   (a) an insertion or deletion in an endogenous slr1125 gene encoding the protein of SEQ ID NO: 2 or SEQ ID NO: 4, such that the host cell is deficient in expression of the endogenous Slr1125 protein of SEQ ID NO: 2 or SEQ ID NO: 4; and
   (b) an insertion or deletion in a gene encoding an endogenous cyanophycin synthetase gene such that the host cell is deficient in production of endogenous cyanophycin.

2. The recombinant cyanobacterial host cell of claim 1, wherein the cyanobacterial host cell is genetically engineered to delete the endogenous slr1125 gene.

3. The recombinant cyanobacterial host cell of claim 1, further comprising a disruption by insertion or deletion of one or more endogenous genes encoding enzymes selected from the group consisting of poly-β-hydroxyalkanoate synthetase, beta ketothiolase, acetoacetyl-CoA reductase, and poly(3-hydroxybutyrate) polymerase.

4. The recombinant cyanobacterial host cell of claim 1, wherein the cyanobacterial host cell is selected from the group consisting of *Synechocystis*, *Arthrospira maxima*, *Synechococcus*, *Trichodesmium*; and *Crocosphaera*.

5. The recombinant cyanobacterial host cell of claim 1, wherein the cyanobacterial host cell is a *Synechocystis* PCC 6803 cell.

6. A method for producing a biomaterial, comprising:
(a) culturing the cyanobacterial host cell of claim 1;
(b) harvesting the cyanobacterial host cell; and
(c) preparing a biomaterial from the harvested cyanobacterial host cell.

7. The method of claim 6, wherein the cyanobacterial host cell has been genetically engineered to delete the endogenous slr1125 gene.

8. The method of claim 6, wherein the biomaterial is polyhydroxyalkanoate (PHA).

9. The method of claim 6, wherein the cyanobacterial host cell is selected from the group consisting of *Synechocystis, Arthrospira maxima, Synechococcus, Trichodesmium*, and *Crocosphaera*.

10. The method of claim 6, wherein the cyanobacterial host cell is *Synechocystis* PCC 6803.

* * * * *

SEQUENCE LISTING

```
<160> NUMBER OF SEQ ID NOS: 39

<210> SEQ ID NO 1
<211> LENGTH: 1200
<212> TYPE: DNA
<213> ORGANISM: Synechocystis sp.

<400> SEQUENCE: 1
atgttgccct tgggtaagga actgcaacag cggggtcata ctgtgaccat gtttggggtg      60
ctagatgccc aagccaaaac cctagcggcc ggtttgaatt ttcaggcgat cgccacaacg     120
gaatttccct tgggagccca ggcagaattt atggctgagt tgggcaaact cagtggcatt     180
aaagctttgc aatacactgt ggccaaaatc acccagaaag cggcggcctt ctttgaggaa     240
gcccctgggg tcatggccaa agccggtgtg gaagttttat tagttgatca agtttcccaa     300 gaaggggggca ccattggcga tcgcctgggt attcccttca tcagtatatg tagcgctgtc     360
gtacttaatc gagagcccac cataccgccc tatgccaccc cttggccata tgatcctagc     420
tggttgggac aattgcggaa tcgccttggc tatggacttt taaatcgggc cactaaaccg     480
attacagcgt taattaatga ctatcgtcag cgttggaatt tacccgccca atctagcccc     540
aatgaccgtt attccccact agcacaaatt agtcagcaac cggcagcgtt tgaatttcct     600
cgggaatgtt taccaagccg tttccatttc actggccctt ttcacagcaa tgtggggcga     660
gatatagctg attttccttg ggagcaattg accgatcagc ccataattta tgcctccctt     720
ggtactattc aaaatcagtt aatgagcacc tttaaaatca ttgccgaagc ctgtatggat     780
ttggatgccc aattgattat ttccctgggg ggagccaagc tagaatcaat gcccgcacta     840
cctggtaatc cctcgttgt taattacgct ccccaactgg aacttctgca agaacagcc      900 cttaccatta cccacgctgg gctcaacacc acgttggaat gcctcaataa tgcagtaccc     960
atggtggcca ttcccattgc caatgatcaa ccgggagtag cggccagaat tgcctgggct    1020
```

```
ggagtgggggg aatttattcc cttgagtaaa ttgaatacga acaatctgcg ggcagccctt   1080
gaaaaagtcc tcactgaaga ttcttataaa agaaatactc tccagcttca acaagcaatt   1140
aaaactgctg gaggtcttac taaagcggcg gatattattg agcaggtaac agcggaggcc   1200
```

<210> SEQ ID NO 2
<211> LENGTH: 402
<212> TYPE: PRT
<213> ORGANISM: Synechocystis

<400> SEQUENCE: 2

```
Met Leu Pro Leu Gly Lys Glu Leu Gln Gln Arg Gly His Thr Val Thr
1               5                   10                  15

Met Phe Gly Val Leu Asp Ala Gln Ala Lys Thr Leu Ala Ala Gly Leu
            20                  25                  30

Asn Phe Gln Ala Ile Ala Thr Thr Glu Phe Pro Leu Gly Ala Gln Ala
        35                  40                  45

Glu Phe Met Ala Glu Leu Gly Lys Leu Ser Gly Ile Lys Ala Leu Gln
    50                  55                  60

Tyr Thr Val Ala Lys Ile Thr Gln Lys Ala Ala Ala Phe Phe Glu Glu
65                  70                  75                  80

Ala Pro Gly Val Met Ala Lys Ala Gly Val Glu Val Leu Leu Val Asp
                85                  90                  95

Gln Val Ser Gln Glu Gly Gly Thr Ile Gly Asp Arg Leu Gly Ile Pro
            100                 105                 110

Phe Ile Ser Ile Cys Ser Ala Val Val Leu Asn Arg Glu Pro Thr Ile
        115                 120                 125

Pro Pro Tyr Ala Thr Pro Trp Pro Tyr Asp Pro Ser Trp Leu Gly Gln
    130                 135                 140

Leu Arg Asn Arg Leu Gly Tyr Gly Leu Leu Asn Arg Ala Thr Lys Pro
145                 150                 155                 160

Ile Thr Ala Leu Ile Asn Asp Tyr Arg Gln Arg Trp Asn Leu Pro Ala
                165                 170                 175

Gln Ser Ser Pro Asn Asp Arg Tyr Ser Pro Leu Ala Gln Ile Ser Gln
            180                 185                 190

Gln Pro Ala Ala Phe Glu Phe Pro Arg Glu Cys Leu Pro Ser Arg Phe
        195                 200                 205

His Phe Thr Gly Pro Phe His Ser Asn Val Gly Arg Asp Ile Ala Asp
    210                 215                 220

Phe Pro Trp Glu Gln Leu Thr Asp Gln Pro Ile Ile Tyr Ala Ser Leu
225                 230                 235                 240

Gly Thr Ile Gln Asn Gln Leu Met Ser Thr Phe Lys Ile Ile Ala Glu
                245                 250                 255

Ala Cys Met Asp Leu Asp Ala Gln Leu Ile Ile Ser Leu Gly Gly Ala
            260                 265                 270

Lys Leu Glu Ser Met Pro Ala Leu Pro Gly Asn Pro Leu Val Val Asn
        275                 280                 285

Tyr Ala Pro Gln Leu Glu Leu Leu Gln Arg Thr Ala Leu Thr Ile Thr
    290                 295                 300

His Ala Gly Leu Asn Thr Thr Leu Glu Cys Leu Asn Asn Ala Val Pro
305                 310                 315                 320

Met Val Ala Ile Pro Ile Ala Asn Asp Gln Pro Gly Val Ala Ala Arg
                325                 330                 335

Ile Ala Trp Ala Gly Val Gly Glu Phe Ile Pro Leu Ser Lys Leu Asn
            340                 345                 350
```

```
Thr Asn Asn Leu Arg Ala Ala Leu Glu Lys Val Leu Thr Glu Asp Ser
        355                 360                 365

Tyr Lys Arg Asn Thr Leu Gln Leu Gln Gln Ala Ile Lys Thr Ala Gly
    370                 375                 380

Gly Leu Thr Lys Ala Ala Asp Ile Ile Glu Gln Val Thr Ala Glu Ala
385                 390                 395                 400

Met Gly

<210> SEQ ID NO 3
<211> LENGTH: 717
<212> TYPE: DNA
<213> ORGANISM: Crocosphaera watsonii

<400> SEQUENCE: 3
ttgagactta agtatcgtca aaagtggcaa ttaggagcag aaacctacac agattcgccc      60
ctagcgattc tctgtcatca acctgctgcc tttgattttc cccgtcaaac cctcccacct     120 cattttact atacaggtcc ctatcatacg agtgaaagtc gtatgtcagt tgattttcct     180
tgggataaac tcacaggaca accctaatt tatgcttcga tgggaacttt gcagaattgt     240
ttaacttatg ttttcgaggc gatcgctggg gcctgtaaag gattagatgc tcaattgctt     300
atttctctag ggggaggttc agaaccggat tctttaccca atcttccagg aaatcctctt     360
gtggtgaaat atgcccctca gttagaactt ttacaaaaag ctgccctaac tattacccac     420
gctggtatga atacaacttt agagtcccta acctatggtg tgccgatgat agctattccc     480
gtgaccaacg atcaaccagg tattgcggcc aggattgctt ggacagggga gggagagatg     540
atcgatttag gtaagttgaa ctccgacaat ttacgcccaa tgattcagcg cgttctaggg     600
gaaaaacgtt atcatgaaaa gtctcaaaaa ttgcagcaag ctattgagaa atcaggggga     660
atagatcaag ctattgccat tattgaacag gctattaacc caatatcagg atcataa       717

<210> SEQ ID NO 4
<211> LENGTH: 238
<212> TYPE: PRT
<213> ORGANISM: Crocosphaera watsonii

<400> SEQUENCE: 4

Met Arg Leu Lys Tyr Arg Gln Lys Trp Gln Leu Gly Ala Glu Thr Tyr
1               5                   10                  15

Thr Asp Ser Pro Leu Ala Ile Leu Cys His Gln Pro Ala Ala Phe Asp
            20                  25                  30

Phe Pro Arg Gln Thr Leu Pro Pro His Phe Tyr Tyr Thr Gly Pro Tyr
        35                  40                  45

His Thr Ser Glu Ser Arg Met Ser Val Asp Phe Pro Trp Asp Lys Leu
    50                  55                  60

Thr Gly Gln Pro Leu Ile Tyr Ala Ser Met Gly Thr Leu Gln Asn Cys
65                  70                  75                  80

Leu Thr Tyr Val Phe Glu Ala Ile Ala Gly Ala Cys Lys Gly Leu Asp
                85                  90                  95

Ala Gln Leu Leu Ile Ser Leu Gly Gly Gly Ser Glu Pro Asp Ser Leu
            100                 105                 110

Pro Asn Leu Pro Gly Asn Pro Leu Val Val Lys Tyr Ala Pro Gln Leu
        115                 120                 125

Glu Leu Leu Gln Lys Ala Ala Leu Thr Ile Thr His Ala Gly Met Asn
    130                 135                 140
```

Thr Thr Leu Glu Ser Leu Thr Tyr Gly Val Pro Met Ile Ala Ile Pro
145                 150                 155                 160

Val Thr Asn Asp Gln Pro Gly Ile Ala Ala Arg Ile Ala Trp Thr Gly
            165                 170                 175

Val Gly Glu Met Ile Asp Leu Gly Lys Leu Asn Ser Asp Asn Leu Arg
            180                 185                 190

Pro Met Ile Gln Arg Val Leu Gly Glu Lys Arg Tyr His Glu Lys Ser
        195                 200                 205

Gln Lys Leu Gln Gln Ala Ile Glu Lys Ser Gly Gly Ile Asp Gln Ala
    210                 215                 220

Ile Ala Ile Ile Glu Gln Ala Ile Asn Pro Ile Ser Gly Ser
225                 230                 235

<210> SEQ ID NO 5
<211> LENGTH: 350
<212> TYPE: DNA
<213> ORGANISM: Crocosphaera watsonii

<400> SEQUENCE: 5
atgcttcctc taggacaagg gttacaaaaa aaaggctatc agatcacctt ttttggcgtt     60
cccgacgcag aaaccaaaat aagagcagct aaacttgatt tttaccctat tggtgcagat    120 attttcctc taggttcaac agaagcttta tttaaaaaac ttagtaaact taaaggtatt    180
cccgccttac aattcaccat caactggttt tatcaatctg cccaaatttt tctggaagaa    240
ggagcaaatg ccctggaaaa aacaggagta gaagcattaa ttgtcgatca aattaatcca    300
gagggaggca cagtagctca attactggat atccctttta taactctttg                350

<210> SEQ ID NO 6
<211> LENGTH: 137
<212> TYPE: PRT
<213> ORGANISM: Crocosphaera watsonii

<400> SEQUENCE: 6

Met Leu Pro Leu Gly Gln Gly Leu Gln Lys Lys Gly Tyr Gln Ile Thr
1               5                   10                  15

Phe Phe Gly Val Pro Asp Ala Glu Thr Lys Ile Arg Ala Ala Lys Leu
            20                  25                  30

Asp Phe Tyr Pro Ile Gly Ala Asp Ile Phe Pro Leu Gly Ser Thr Glu
        35                  40                  45

Ala Leu Phe Lys Lys Leu Ser Lys Leu Lys Gly Ile Pro Ala Leu Gln
    50                  55                  60

Phe Thr Ile Asn Trp Phe Tyr Gln Ser Ala Gln Ile Phe Leu Glu Glu
65                  70                  75                  80

Gly Ala Asn Ala Leu Glu Lys Thr Gly Val Glu Ala Leu Ile Val Asp
                85                  90                  95

Gln Ile Asn Pro Glu Gly Gly Thr Val Ala Gln Leu Leu Asp Ile Pro
            100                 105                 110

Phe Ile Thr Leu Cys Ser Ala Leu Pro Phe Asn Gln Glu Pro Gly Cys
        115                 120                 125

Asp Ser Met Ser Gln Lys Ala Asp Ile
    130                 135

<210> SEQ ID NO 7
<211> LENGTH: 1278
<212> TYPE: DNA
<213> ORGANISM: Trichodesmium erythraeum

<400> SEQUENCE: 7

```
ttatatagtt cctgttaaaa ctggtttacc tgttgatact gcctgttcaa taatatcagc    60
agcacgagtg actccacctg ctcgtttaat tgctttctgt aatctcaaag cattttgctt   120
atatgacggt tgtgtgagca cctgagaaat agctgttcgt aaccgaggta ctgttaaacg   180
tttcagtgtt atcgctactc cagctccagc ccaagctatt cgtgccgcta ctcctggttg   240
atcgttagca ataggaatag caaccattgg tactgcatta cttaaacatt ctagagttgt   300
attcatacct gcatgagtaa tagtgagagt agcttttttgc agtatttcta attggggtgc   360
atattcaaca actagaggat tcctgctaa gttgggtaga gattctggag tggcagaacc   420
tcccagagaa ataactaact gagcatccaa cccctcacaa gctgctgtaa tttgataaaa   480
tacctcaacc aaacgatttt gtatagttcc catagaggca taaattaaag gtttacctgt   540
caactgttcc caaggaaagg aaacaggttc tctagtacct gaataatgat aaggtcctgt   600
gaaatgaaaa cacttaggta aatttctct gggaaattct aactcagcag gttgctgact   660
aatttgagcc agtagagaat aagcatcatt ggggtcagag tacaaaggta aattccattg   720
acgacgatac tcagctacta ccttgttaat aggtttgcct aagatttgat agaaactcca   780
agtagctcta ttacgcagtt ttgcccacca ggcggggtta tatttccagt tgcttacagg   840
gtggggaaca ttctcatctt gattgagtac cagtgcacta caaatagtaa taaagggaat   900
gtctagaaaa tcccctatag attctcctaa tgaagcctgg tcgattaaca aagcatctac   960
accagcattt tgatgactt gcggagcatc ccgaagcaaa acatttgtcc agtctttaa  1020
tagtgtaatt gtatagcgaa atgcagctaa cccgctgagt ttactcaggt gatttaaagc  1080
ttctgctgtg ctgcccttag aatattcttc cgtgccatag caacaaatt ctaatcctgc  1140
tgctagtgtc ttagcttcag cgtcaagtat ccctatcgtc gtgacacgat gaccacgcct  1200
ttttaattct tgtcctatgg gaagcattgg atttaggtgt cctgtcaatg ccggacaaat  1260
cagaccaaaa tgagtcat                                                1278
```

<210> SEQ ID NO 8
<211> LENGTH: 425
<212> TYPE: PRT
<213> ORGANISM: Trichodesmium erythraeum

<400> SEQUENCE: 8

```
Met Thr His Phe Gly Leu Ile Cys Pro Ala Leu Thr Gly His Leu Asn
1               5                   10                  15

Pro Met Leu Pro Ile Gly Gln Glu Leu Lys Arg Arg Gly His Arg Val
            20                  25                  30

Thr Thr Ile Gly Ile Leu Asp Ala Glu Ala Lys Thr Leu Ala Ala Gly
        35                  40                  45

Leu Glu Phe Val Ala Tyr Gly Thr Glu Glu Tyr Ser Lys Gly Ser Thr
    50                  55                  60

Ala Glu Ala Leu Asn His Leu Ser Lys Leu Ser Gly Leu Ala Ala Phe
65                  70                  75                  80

Arg Tyr Thr Ile Thr Leu Leu Lys Asp Trp Thr Asn Val Leu Leu Arg
                85                  90                  95

Asp Ala Pro Gln Val Ile Lys Asn Ala Gly Val Asp Ala Leu Leu Ile
            100                 105                 110

Asp Gln Ala Ser Leu Gly Glu Ser Ile Gly Asp Phe Leu Asp Ile Pro
        115                 120                 125

Phe Ile Thr Ile Cys Ser Ala Leu Val Leu Asn Gln Asp Glu Asn Val
```

```
            130                 135                 140
Pro His Pro Val Ser Asn Trp Lys Tyr Asn Pro Ala Trp Trp Ala Lys
145                 150                 155                 160

Leu Arg Asn Arg Ala Thr Trp Ser Phe Tyr Gln Ile Leu Gly Lys Pro
                165                 170                 175

Ile Asn Lys Val Val Ala Glu Tyr Arg Arg Gln Trp Asn Leu Pro Leu
            180                 185                 190

Tyr Ser Asp Pro Asn Asp Ala Tyr Ser Leu Leu Ala Gln Ile Ser Gln
        195                 200                 205

Gln Pro Ala Glu Leu Glu Phe Pro Arg Glu Asn Leu Pro Lys Cys Phe
    210                 215                 220

His Phe Thr Gly Pro Tyr His Tyr Ser Gly Thr Arg Glu Pro Val Ser
225                 230                 235                 240

Phe Pro Trp Glu Gln Leu Thr Gly Lys Pro Leu Ile Tyr Ala Ser Met
                245                 250                 255

Gly Thr Ile Gln Asn Arg Leu Val Glu Val Phe Tyr Gln Ile Thr Ala
            260                 265                 270

Ala Cys Glu Gly Leu Asp Ala Gln Leu Val Ile Ser Leu Gly Gly Ser
        275                 280                 285

Ala Thr Pro Glu Ser Leu Pro Asn Leu Ala Gly Asn Pro Leu Val Val
    290                 295                 300

Glu Tyr Ala Pro Gln Leu Glu Ile Leu Gln Lys Ala Thr Leu Thr Ile
305                 310                 315                 320

Thr His Ala Gly Met Asn Thr Thr Leu Glu Cys Leu Ser Asn Ala Val
                325                 330                 335

Pro Met Val Ala Ile Pro Ile Ala Asn Asp Gln Pro Gly Val Ala Ala
            340                 345                 350

Arg Ile Ala Trp Ala Gly Ala Gly Val Ala Ile Thr Leu Lys Arg Leu
        355                 360                 365

Thr Val Pro Arg Leu Arg Thr Ala Ile Ser Gln Val Leu Thr Gln Pro
    370                 375                 380

Ser Tyr Lys Gln Asn Ala Leu Arg Leu Gln Lys Ala Ile Lys Arg Ala
385                 390                 395                 400

Gly Gly Val Thr Arg Ala Ala Asp Ile Ile Glu Gln Ala Val Ser Thr
                405                 410                 415

Gly Lys Pro Val Leu Thr Gly Thr Ile
            420                 425

<210> SEQ ID NO 9
<211> LENGTH: 400
<212> TYPE: DNA
<213> ORGANISM: Artificial
<220> FEATURE:
<223> OTHER INFORMATION: Synthetic

<400> SEQUENCE: 9
agcgacttca gcccacaaaa aacaccactg ggcctactgg gctattccca ttatcatcta      60
cattgaaggg atagcaagct aattttatg acggcgatcg ccaaaaacaa agaaaattca     120
gcaattaccg tgggtagcaa aaatccca tctaaagttc agtaaatata gctagaacaa      180
ccaagcattt tcggcaaagt actattcaga tagaacgaga aatgagcttg ttctatccgc     240
ccggggctga ggctgtataa tctacgacgg gctgtcaaac attgtgatac catgggcaga     300 agaaggaaa aacgtccctg atcgcctttt tgggcacgga gtagggcgtt accccggccc      360
gttcaaccac aagtccctat agatacaatc gccaagaagt                           400
```

<210> SEQ ID NO 10
<211> LENGTH: 558
<212> TYPE: PRT
<213> ORGANISM: Synechocystis

<400> SEQUENCE: 10

| Met | Phe | Thr | Ile | Ala | Leu | Ala | Gln | Leu | Asn | Pro | Thr | Ile | Gly | Ala | Ile |
|---|---|---|---|---|---|---|---|---|---|---|---|---|---|---|---|
| 1 | | | | 5 | | | | | 10 | | | | | 15 | |

Ala Glu Asn Ala Glu Lys Ile Val Thr Ala Ala Leu Gln Ala Gln Ala
              20                  25                  30

Arg Gly Ala Asp Leu Leu Leu Thr Pro Glu Leu Ala Leu Cys Gly Tyr
         35                  40                  45

Pro Pro Lys Asp Leu Leu Leu Asn Pro Ser Phe Val Glu Gln Leu Glu
 50                  55                  60

Glu Glu Leu Gln Trp Leu Ala Glu Lys Met Pro Pro Ser Ile Ala Ile
65                  70                  75                  80

Leu Val Gly Thr Val Thr Pro His His Gln Ala Glu Arg Gln Gly Gln
                 85                  90                  95

Lys Lys Leu Trp Asn Ser Ala Val Leu Ile Glu Gln Gly Gln Ile Lys
            100                 105                 110

Gln Trp Phe His Lys Cys Leu Leu Pro Thr Tyr Asp Val Phe Asp Glu
        115                 120                 125

Asp Arg Tyr Phe Ala Ser Ala Lys Ser Glu Tyr Phe Ile Tyr Lys
    130                 135                 140

Asn Val Lys Ile Gly Val Thr Ile Cys Glu Asp Leu Trp Asn Asp Glu
145                 150                 155                 160

Ala Phe Trp Gly Gln Lys Phe Tyr Gln Val Asn Pro Leu Met Asp Leu
                165                 170                 175

Ile Asp Gln Gly Val Asn Leu Val Val Asn Leu Ser Ala Ser Pro Tyr
            180                 185                 190

Ser Cys Gly Lys His Tyr Leu Arg Glu Ser Leu Ile Ser His Ser Ala
        195                 200                 205

Lys Arg Phe Asn Val Pro Leu Ile Tyr Val Asn Gln Val Gly Gly Asn
    210                 215                 220

Asp Asp Leu Ile Phe Asp Gly Gly Ser Phe Ala Val Asn Ser Gln Gly
225                 230                 235                 240

Lys Ile Ile Gly Arg Ser Pro Leu Phe Gln Glu Asp Leu Ala Leu Leu
                245                 250                 255

Ser Tyr Asp Leu Ser Ser Gly Glu Leu Thr Gly Gln Lys Leu Ala Ser
            260                 265                 270

Leu Pro Met Val Asp Thr Glu Glu Leu Trp Gln Ala Leu Val Leu Gly
        275                 280                 285

Val Gly Asp Tyr Leu His Lys Cys Gly Phe Ser Lys Ala Ile Leu Gly
    290                 295                 300

Leu Ser Gly Gly Ile Asp Ser Ser Leu Val Ala Ala Ile Ala Val Glu
305                 310                 315                 320

Ala Leu Gly Lys Glu Asn Val Leu Gly Ile Leu Met Pro Ser Pro Tyr
                325                 330                 335

Ser Ser Asp His Ser Ile Gln Asp Ala Leu Ala Leu Ala Lys Asn Leu
            340                 345                 350

Gly Met Asn Thr Gln Thr Ile Pro Ile Gly Pro Ile Met Ala Thr Tyr
        355                 360                 365

Asp Gln Ala Leu Val Pro Leu Phe Gln Asp Ala Pro Phe Gly Leu Ala

```
            370                 375                 380
Glu Glu Asn Leu Gln Ser Arg Ile Arg Gly Asn Leu Leu Met Ala Ile
385                 390                 395                 400

Ala Asn Lys Phe Gly His Leu Leu Ser Thr Gly Asn Lys Ser Glu
            405                 410                 415

Leu Ala Val Gly Tyr Cys Thr Leu Tyr Gly Asp Met Asn Gly Gly Leu
            420                 425                 430

Ala Ala Ile Ala Asp Val Pro Lys Thr Gln Val Phe Glu Leu Cys Arg
            435                 440                 445

Trp Leu Asn Arg Glu Gln Thr Ile Ile Pro Pro Ser Val Leu Thr Lys
            450                 455                 460

Pro Pro Ser Ala Glu Leu Lys Pro Gly Gln Val Asp Thr Asp Ser Leu
465                 470                 475                 480

Pro Pro Tyr Asp Val Leu Asp Gly Ile Leu Gly Arg Leu Val Glu Lys
            485                 490                 495

His Gln Ser Pro Gln Glu Ile Ile Asn Ala Gly Phe Glu Arg Glu Val
            500                 505                 510

Val Leu Lys Ile Cys Gln Leu Val Gln Lys Ser Glu Phe Lys Arg Arg
            515                 520                 525

Gln Ala Ala Pro Gly Leu Lys Val Thr Asp Arg Ala Phe Gly Ser Gly
            530                 535                 540

Trp Arg Met Pro Ile Ala Gln Ala Phe His Pro Gln Gly Ser
545                 550                 555

<210> SEQ ID NO 11
<211> LENGTH: 562
<212> TYPE: PRT
<213> ORGANISM: CROCOSPHAERA WATSON II

<400> SEQUENCE: 11

Met Lys Ile Ala Ile Ala Gln Leu Asn Pro Ile Ile Gly Asp Ile Glu
1               5                   10                  15

Asn Asn Ala Gln Asn Ile Cys Lys Ala Ala Glu Ile Ala Val Gln Gly
                20                  25                  30

Glu Ala Gln Leu Leu Leu Thr Pro Glu Leu Ser Leu Cys Gly Tyr Pro
            35                  40                  45

Pro Lys Asp Leu Leu Leu Asn Ala Ser Phe Val Glu Met Leu Trp Ala
        50                  55                  60

Glu Leu Glu Lys Leu Ala Lys Thr Ile Pro Asn Asn Leu Thr Val Leu
65                  70                  75                  80

Val Gly Thr Val Ile Glu Asn Pro Asn Ala Tyr Asn Glu Gly Lys Lys
                85                  90                  95

Pro Leu Phe Asn Ser Ile Val Leu Ile Glu Asn Gln Thr Ile Lys Gln
            100                 105                 110

Ile Phe His Lys Arg Leu Leu Pro Thr Tyr Asp Val Phe Asp Glu Asp
        115                 120                 125

Arg Tyr Phe Glu Pro Gly Lys Glu Ser Asn Phe Phe Gln Leu Ser Ser
    130                 135                 140

Asn Ile Pro Asn Thr Lys Pro Leu Lys Ile Gly Val Thr Ile Cys Glu
145                 150                 155                 160

Asp Leu Trp Asn Asp Glu Glu Phe Trp Gly Lys Arg Asn Tyr Glu Asn
                165                 170                 175

Asn Pro Ile Gln Asp Leu Val Lys Tyr Gly Val Asp Leu Val Val Asn
            180                 185                 190
```

```
Leu Ser Ala Ser Pro Tyr Ser Val Gly Lys Gln Lys Ile Arg Glu Ala
            195                 200                 205

Met Leu Lys His Ser Ala Glu Arg Tyr Gln Val Pro Ile Ile Tyr Thr
210                 215                 220

Asn Gln Val Gly Gly Asn Asp Asp Leu Ile Phe Asp Gly Asn Ser Phe
225                 230                 235                 240

Ala Val Ser Arg Lys Gly Glu Ile Ser Leu Arg Ala Lys Gly Tyr Gln
                245                 250                 255

Thr Ala Ile Glu Val Ile Glu Tyr Asp Gln Asn Asn Glu Asp Leu Lys
            260                 265                 270

Thr Ser Tyr Ile Ala Asn Ser Ile Glu Thr Glu Glu Glu Ile Trp
            275                 280                 285

Ser Ser Leu Val Leu Gly Leu Lys Asp Tyr Ala Thr Lys Cys Gly Phe
290                 295                 300

Ser Lys Ala Ile Leu Gly Leu Ser Gly Gly Ile Asp Ser Ser Leu Val
305                 310                 315                 320

Ala Ala Ile Ala Val Glu Ala Leu Gly Lys Glu Asn Val Leu Gly Ile
                325                 330                 335

Leu Met Pro Ser Pro Tyr Ser Ser Ser His Ser Ile Ser Asp Gly Glu
            340                 345                 350

Ala Leu Val Asn Asn Leu Gly Ile Asn Ser His Thr Leu Ala Ile Gly
            355                 360                 365

Asp Val Met Lys Ala Tyr Asp Leu Leu Leu Glu Pro Leu Phe Lys Asn
            370                 375                 380

Thr Glu Phe Gly Val Ala Glu Glu Asn Leu Gln Ser Arg Ile Arg Gly
385                 390                 395                 400

Asn Leu Leu Met Ala Ile Ala Asn Lys Phe Gly His Leu Leu Leu Ser
                405                 410                 415

Thr Gly Asn Lys Ser Glu Met Ala Val Gly Tyr Cys Thr Leu Tyr Gly
            420                 425                 430

Asp Met Asn Gly Gly Leu Ala Val Ile Ser Asp Val Pro Lys Thr Arg
            435                 440                 445

Val Phe Ser Leu Cys Lys Trp Leu Asn Arg His Gln Glu Val Ile Pro
450                 455                 460

His Asn Ile Ile Val Lys Pro Pro Ser Ala Glu Leu Lys Pro Asp Gln
465                 470                 475                 480

Leu Asp Gln Asp Ser Leu Pro Ala Tyr Asp Ile Leu Asp Ala Ile Leu
                485                 490                 495

Asp Arg Leu Ile His Arg His Gln Ser Val Lys Glu Ile Thr Ala Ala
            500                 505                 510

Gly Phe Asp Tyr Asp Thr Ile Cys Lys Ile Val Lys Leu Val Asn Arg
            515                 520                 525

Ala Glu Phe Lys Arg Lys Gln Ala Pro Pro Gly Leu Lys Val Ser Asp
            530                 535                 540

Arg Ala Phe Gly Thr Gly Trp Arg Met Pro Ile Ala Ser Arg Arg Lys
545                 550                 555                 560

Leu Asp

<210> SEQ ID NO 12
<211> LENGTH: 584
<212> TYPE: PRT
<213> ORGANISM: TRICHODESMIUM ERYTHRAEUM

<400> SEQUENCE: 12
```

-continued

```
Met Lys Ile Ala Ile Ala Gln Leu Asn Pro Val Ile Gly Asp Ile Ser
1               5                   10                  15

Gly Asn Ala Lys Leu Ile Leu Asp Ala Ala Gln Lys Ala Lys Lys Leu
            20                  25                  30

Asp Ala Lys Leu Met Ile Thr Pro Glu Leu Ser Leu Ile Gly Tyr Pro
        35                  40                  45

Pro Arg Asp Leu Leu Ile Tyr Pro Ser Leu Ile Glu Ala Ala Val Leu
    50                  55                  60

Glu Leu Glu Asn Leu Ala Lys Tyr Leu Pro Ser Glu Ile Ala Val Leu
65                  70                  75                  80

Val Gly Thr Val Thr Phe Asn Tyr Gln Ala Ala Asn Thr Gly Glu Lys
                85                  90                  95

Ser Leu Phe Asn Ser Ala Val Leu Leu Thr Asn Gly Glu Ile Lys Gln
            100                 105                 110

Val Phe His Lys Gln Leu Leu Pro Thr Tyr Asp Val Phe Asp Glu Asp
        115                 120                 125

Arg Tyr Phe Glu Pro Gly Lys Thr Arg Asp Phe Phe Thr Leu Glu Asn
    130                 135                 140

Tyr Ser Asn Ser Ser Glu Asn Leu Ala Lys Val Gly Val Thr Ile Cys
145                 150                 155                 160

Glu Asp Leu Trp Asn Asp Glu Ala Phe Trp Gly Lys Arg Asn Tyr Ala
                165                 170                 175

Tyr Asp Pro Met Lys Glu Leu Ala Ala Gln Lys Val Asp Phe Val Ile
            180                 185                 190

Asn Met Ser Ala Ser Pro Tyr Gln Thr Gly Lys Gln Lys Leu Arg Glu
        195                 200                 205

Ala Met Leu Lys His Ser Thr Asn Cys Tyr Gln Ile Pro Ile Ile Tyr
    210                 215                 220

Val Asn Gln Val Gly Gly Asn Asp Asp Leu Ile Phe Asp Gly Cys Ser
225                 230                 235                 240

Val Val Phe Asn Gly Ala Gly Asn Val Val Tyr Arg Ala Gln Ala Phe
                245                 250                 255

Glu Thr Ser Leu Ala Val Val Glu Phe Asn Ser Ala Lys Lys Asp Phe
            260                 265                 270

Ile Ser Val Asp Phe Lys Ser Ile Asn Leu Pro Glu Ser Glu Asp Glu
        275                 280                 285

Glu Ile Trp Ser Ala Leu Val Leu Gly Leu Arg Asp Tyr Val Gln Lys
    290                 295                 300

Cys Gly Phe Ser Lys Val Val Leu Gly Leu Ser Gly Gly Ile Asp Ser
305                 310                 315                 320

Ala Leu Val Ala Ala Ile Ala Thr Ala Ala Leu Gly Lys Glu Asn Val
                325                 330                 335

Phe Ala Ile Leu Met Pro Ser Pro Tyr Ser Ser Glu His Ser Val Lys
            340                 345                 350

Asp Ala Leu Glu Leu Ala Glu Asn Leu Gly Ile Ala Lys Gln Ile Ile
        355                 360                 365

Ser Ile Glu Asn Leu Met Lys Asp Tyr Asp Asn Ser Leu Ser Ser Leu
    370                 375                 380

Phe Thr Gly Thr Asn Phe Gly Ile Ala Glu Glu Asn Ile Gln Ser Arg
385                 390                 395                 400

Ile Arg Gly Asn Leu Leu Met Ala Ile Ser Asn Lys Phe Gly Tyr Leu
                405                 410                 415

Leu Leu Ser Thr Gly Asn Lys Ser Glu Met Ala Val Gly Tyr Cys Thr
```

```
                420              425              430
Leu Tyr Gly Asp Met Asn Gly Gly Leu Ala Val Ile Ser Asp Val Pro
            435              440              445

Lys Thr Arg Val Tyr Ser Leu Cys Gln Trp Leu Asn Glu Gln Thr Val
        450              455              460

Asn Asn Asn Lys Lys Phe Ser Gly Ser Gln Asn Leu Leu Met Thr Glu
465              470              475              480

Lys Gln Asn Ile Ile Pro Lys Asn Ile Leu Thr Lys Ala Pro Ser Ala
            485              490              495

Glu Leu Lys Glu Gly Gln Lys Asp Glu Asp Ser Leu Pro Ala Tyr Glu
        500              505              510

Val Leu Asp Asp Ile Leu Phe Arg Leu Val Glu Lys Cys Glu Ser Leu
        515              520              525

Asp Lys Ile Ile Ala Ala Gly His Asp Leu Glu Val Val Asn Lys Val
        530              535              540

Val Lys Leu Val Met Arg Ala Glu Phe Lys Arg Arg Gln Ala Pro Pro
545              550              555              560

Gly Leu Lys Ile Ser Thr Arg Ala Phe Gly Thr Gly Trp Arg Met Pro
            565              570              575

Ile Ala Lys Lys Leu Val Ile Asn
            580

<210> SEQ ID NO 13
<211> LENGTH: 1677
<212> TYPE: DNA
<213> ORGANISM: Synechocystis

<400> SEQUENCE: 13
atgtttacca ttgcccttgc ccagcttaat cccaccattg gggcgatcgc cgagaatgcc      60
gaaaaaattg tcacggcagc cctgcaagcc caggcaaggg gagctgattt actattaacg     120
ccggaattag ccctctgtgg ttatcccccc aaggatttgt tacttaatcc aagttttgtc     180
gaacaactgg aagaagagtt acaatggctg gcggaaaaaa tgcctccttc tatagcaatt     240
ttagtgggca ctgttactcc ccaccaccag gcagaacgcc aaggacaaaa aaaactttgg     300
aatagtgcag tattaattga acaaggacag ataaagcagt ggtttcataa atgtctccta     360
cccacctatg acgtatttga tgaagaccgt tattttgcct cggctgccaa gagtgaatat     420
tttatctata aaaacgtcaa aattggtgtg actatttgtg aagatttgtg gaatgacgag     480
gcttttgggg acaaaaaatt ttatcaagtt aaccccctca tggatttgat tgatcagggc     540
gtgaatttag ttgttaacct atcagcttct ccctacagtt gtggcaagca ttacctgcga     600
gaatccttga ttagccacag tgccaagaga tttaatgtgc ctttgattta tgttaaccaa     660 gtgggggggca atgatgatct cattttttgat gggggtagtt ttgctgtcaa tagccaaggc     720
aaaattattg gcgatcacc gttatttcaa gaagacttag ccctgttaag ttatgactta     780
agtagtgggg agttaactgg gcaaaagtta gctagtttac ctatggtgga taccgaagaa     840
ttgtggcaag ctctggtgtt gggggtggga gactacctcc acaaatgcgg ttttagtaag     900 gcaatttttag gtctgagcgg cggcattgac tcttccctag tggcggccat tgctgtggaa     960
gctttgggca agaaaaatgt gctgggaatt ttgatgcctt ctccctacag ttctgaccat    1020
tctattcagg atgccttggc cttggcaaag aatttaggta tgaataccca aactattccc    1080
attgggccga ttatgccac ctatgaccag gccctagtac ccttttttca agatgccccc    1140
tttggccttg ccgaagaaaa tctccagtcc cgcatccggg caacctcct gatggcgatc    1200
```

```
gccaataaat ttggccatct actcctcagc actggcaata aatcggaatt agcggtgggt      1260
tactgcaccc tctacgggga catgaacggt ggcctagcgg cgatcgccga cgtccccaaa      1320
acccaagtat ttgaactatg ccgctggctc aaccgggaac aaaccatcat tccccccagc      1380
gttctgacta aaccgcccag cgccgaactc aaaccagggc aagtagacac cgactccctt      1440
cccccctacg atgtcttgga cggcattctt gggagattag tcgaaaaaca tcagtctccc      1500
caggaaatca tcaacgcagg ctttgagcgg gaagtcgtac taaaaatttg ccaactagtg      1560
caaaagtcag agttcaaacg tcgtcaggcc gccccgggac tgaaagtcac agatcgagcc      1620
tttggcagtg gttggcgcat gcccattgcc caagctttcc atccccaagg cagttaa        1677

<210> SEQ ID NO 14
<211> LENGTH: 1689
<212> TYPE: DNA
<213> ORGANISM: CROCOSPHAERA WATSONII

<400> SEQUENCE: 14
atgaaaattg cgatcgctca acttaatccg attattggtg atattgaaaa caacgctcaa       60
aatatctgta aagcggcaga aatagctgta caaggagaag cacaattatt attaaccccct     120 gaactctctc tatgtggcta tcctcccaaa gatttactat aaatgctag ttttgtagaa       180 atgttatggg cagaattaga aaaactagct aaaacaatcc ccataatttt aactgtttta      240
gtgggaacag ttatcgaaaa tcctaatgct tataatgagg gaaagaaacc cttgtttaac      300
agtattgtat taatcgaaaa tcaaactata aaacaaattt ttcataaacg gcttttaccc      360
acgtatgatg ttttttgatga agatagatat tttgaaccag gaaaagaaag taatttcttt      420 caattatcttt ctaacattcc caatacaaaa cctcttaaaa ttggggttac aatatgcgaa     480
gatttatgga atgatgaaga attttggggt aaaagaaact atgaaaataa ccctatacaa      540
gacttggtta aatatggggt agatttagtg gttaatttat ctgcttctcc ttatagtgtt      600
ggtaaacaaa agataagaga agctatgtta aagcatagtg cagaacgtta tcaggttccc      660
attatttata ctaaccaagt aggaggaaat gatgaaccta tttttgatgg taatagtttt      720
gctgttagca gaaaaggcga aattagctta cgtgcaaaag gatatcaaac tgccatagaa      780
gttattgaat atgaccaaaa taatgaagac ttaaaaaacca gttatattgc taattctata     840
gaaacagaag aagaggaaat ctggtcatct ttagtgttag gattaaaaga ttatgctact      900
aaatgtggct tttctaaagc tattttaggg ttaagtggtg gtattgattc atctttagtt      960
gctgctattg ctgttgaagc attaggtaag gaaaatgtgt taggaatatt aatgccatca     1020
ccctatagtt caagtcattc tattagtgat ggagaagcgt tagttaataa cttaggaatt      1080
aatagtcata ctttagctat tggggatgtt atgaaagctt atgatttgtt gttagaaccc      1140
ttatttaaaa atacagagtt tggggttgca gaagaaaatt tacaatccag aattcgtggt      1200
aatttgttga tggcgatcgc caataagttc ggacatttac tattatcaac cggaaataaa      1260
tcagaaatgg cagtaggtta ctgtaccta tacgggata tgaatggggg tttagcggtt      1320
atttcagatg ttcctaagac ccgtgttttt agcctgtgta agtggttaaa ccgacatcaa     1380
gaggtaatac cccataatat catagttaag cccctagtg ccgaattaaa gcccgatcaa     1440
ctggatcaag attctttacc agcttatgac attttagatg ctattctcga cagattaatt     1500
catcgtcatc aatctgtaaa agaaattaca gcagcagggt ttgattatga tacaatttgt     1560
aagatagtaa aattggtgaa ccgtgcagaa tttaagcgta acaggctcc tcctggatta     1620
```

```
aaagtaagcg atcgtgcatt tggtacaggt tggagaatgc ccattgctag tcgtagaaaa    1680
ttagattaa                                                            1689

<210> SEQ ID NO 15
<211> LENGTH: 1755
<212> TYPE: DNA
<213> ORGANISM: TRICHODESMIUM ERYTHRAEUM

<400> SEQUENCE: 15
atgaaaattg caattgctca acttaatcct gtgattggtg atatttcagg caatgccaaa      60
ttaattttgg atgctgcaca aaaagcaaaa aaattagatg ctaagttgat gataactcca     120
gaattatcat taataggtta tcccccacga gatttattaa tttatcctag tttaattgaa     180
gctgcagttc tagaattaga aaatttagcc aaatatttac catcagaaat agccgtttta     240
gtaggaactg taacctttaa ttatcaagcc gctaatacag gagaaaaatc actatttaat     300
agtgcagttt tattaaccaa tggcgaaatc aaacaagtat tcataaaaca acttttacct     360
acttatgatg tatttgatga agaccgatat tttgaacctg gtaaaactag ggatttttc     420 acgttagaaa attattctaa cagctcagaa aatttagcta agtaggtgt aactatctgc      480 gaagacttat ggaatgatga ggctttttgg ggaaaacgaa attatgctta tgacccgatg     540
aaagaattag cagcacaaaa agttgatttt gtgattaata tgtcagcttc tccctatcaa     600
actggaaaac aaaaattgcg agaagcaatg ttaaaacata gtacaaattg ttatcaaata     660
ccaattattt atgtcaatca gtgggtggt aatgatgatt taatttttga tggttgtagt     720
gtagttttta atggtgctgg aaatgtggtt tatcgtgctc aagcttttga dacaagtttg     780
gcagttgtag aatttaattc agcaaaaaaa gatttcattt cagtagattt taaaagtata     840

aatttgccag aaagtgagga tgaagaaatt tggtctgctt tggttttagg cctaagagat     900
tatgtacaaa agtgtggttt ttctaagtt gttctgggtt taagtggagg aatagactca     960
gctttagttg cagcgatcgc tactgctgca ttaggaaaag aaaatgtctt tgctattttg    1020
atgccttctc cctacagttc tgagcattcg gtaaagatg ctttagaatt agcagaaaat    1080

ttgggtattg ctaaacaaat tatatctatt gagaatttaa tgaaggatta tgataatagt    1140

ctgtcaagtt tatttacagg tacaaatttt ggtattgctg aagagaatat tcaatctcgg    1200

atcgtggaa аттттатtaат ggctatttct aataagtttg gttatttact ttatctaca    1260 ggcaataagt cagaaatggc tgttggttat тgтактстт atggtgatat gaatggtgga    1320

ttagcagtaa tttcagatgt gccgaaaact cgggtttatt ctttatgtca gtggttgaat    1380
gaacagacag ttaataacaa taaaaaattc tctggatccc aaaacttact aatgactgaa    1440
aagcaaaata ttattcccaa aaatatactg acaaaagctc ccagtgctga gttaaaagaa    1500
ggtcaaaagg atgaggattc tttacctgct tatgaagtct agatgatat tttatttagg    1560

ttagtagaaa agtgcgaatc tttagacaaa attattgctg caggacatga tttagaggtg    1620
gtaaataagg tagtaaaatt agtcatgagg gcagaattta acgtagaca agcaccccca    1680 ggtttgaaaa ttagtactcg cgcttttggc acaggttggc ggatgcctat tgctaaaaaa    1740

ttagttatta actga                                                     1755

<210> SEQ ID NO 16
<211> LENGTH: 307
<212> TYPE: PRT
<213> ORGANISM: Synechocystis sp.

<400> SEQUENCE: 16
```

```
Met Glu Leu Lys Gln Val Ile Ile Ala His Lys Ala Gly His Asn Glu
1               5                   10                  15

Ser Lys Thr Tyr Ala Glu Arg Cys Ala Arg Glu Leu Glu Ala Arg Gly
            20                  25                  30

Cys Lys Val Leu Met Gly Pro Ser Gly Ile Lys Asp Asn Pro Tyr Pro
        35                  40                  45

Val Phe Leu Ala Ser Ala Thr Glu Lys Ile Asp Leu Ala Leu Val Leu
    50                  55                  60

Gly Gly Asp Gly Thr Thr Leu Ala Ala Ala Arg His Leu Ser Pro Glu
65                  70                  75                  80

Gly Ile Pro Ile Leu Ser Val Asn Val Gly His Leu Gly Phe Leu
                85                  90                  95

Thr Glu Pro Phe Asp Val Phe Gln Asp Thr Gln Lys Val Trp Asp Arg
                100                 105                 110

Leu Asn Gln Asp Arg Tyr Ala Val Ser Gln Arg Met Met Leu Ala Ala
            115                 120                 125

Ser Leu Phe Glu Gly Asp Arg Arg Asp Pro Gln Met Val Gly Glu Thr
130                 135                 140

Tyr Tyr Cys Leu Asn Glu Met Cys Ile Lys Pro Ala Ser Ile Asp Arg
145                 150                 155                 160

Met Pro Thr Ala Ile Ile Glu Val Glu Val Asp Gly Glu Leu Ile Asp
                165                 170                 175

Gln Tyr Gln Cys Asp Gly Leu Leu Val Ala Thr Pro Thr Gly Ser Thr
            180                 185                 190

Cys Tyr Thr Ser Ser Ala Asn Gly Pro Ile Leu His Pro Gly Met Asp
        195                 200                 205

Ala Ile Val Ile Thr Pro Ile Cys Pro Leu Ser Leu Ser Ser Arg Pro
    210                 215                 220

Ile Val Ile Pro Pro Gly Ser Ser Val Asn Ile Trp Pro Leu Gly Asp
225                 230                 235                 240

Phe Glu Leu Asn Thr Lys Leu Trp Thr Asp Gly Ser Leu Ala Thr Gly
                245                 250                 255

Val Trp Pro Gly Gln Arg Val Gly Val Trp Met Ala His Arg Ala Ala
            260                 265                 270

Gln Phe Ile Leu Leu Arg Glu Ser Tyr Ser Phe Tyr Lys Thr Leu Arg
        275                 280                 285

Asp Lys Leu Gln Trp Ala Gly Ala Arg Phe Leu Tyr Asp Gly Asn Asn
    290                 295                 300

Lys Val Asn
305

<210> SEQ ID NO 17
<211> LENGTH: 924
<212> TYPE: DNA
<213> ORGANISM: Synechocystis sp.

<400> SEQUENCE: 17
gtggaactga aacaggtgat cattgcccat aaagccgggc acaatgaaag caaaacctat      60
gccgaacggt gtgccaggga actggaagct aggggttgta aggtgctgat gggccccagt     120
ggcattaaag acaatcccta tccagtgttt ttggcttccg ccacagaaaa aatagatttg     180
gctttggttt tagggggaga tggcactacc ctagcggcgg ccaggcattt atccccgaa      240 ggcattccca ttttgtctgt taacgtgggc gggcatctag gatttttgac ggaaccattc     300
```

-continued

```
gatgtgttcc aggatactca aaggtgtgg gaccgtctca accaagaccg ctatgctgtt      360
tcccaacgca tgatgctagc ggccagttta tttgaaggcg atcgccggga tccccagatg      420 gtggggaaa cctactactg tctgaacgaa atgtgcatca aaccggccag tattgaccgg       480
atgcccacgg ccatcatcga agtggaagtg gatggggagt taattgatca gtatcagtgc      540
gacggtcttt tggtcgccac ccctacgggt tctacttgct atacatcctc tgccaatggc      600
cccatcttgc accctggcat ggacgccatt gtcattactc ccatttgtcc cctgagctta      660
tccagccgcc ccattgtcat tcccctggc tcttcggtaa acatttggcc cctgggggat       720
tttgagttaa atactaaact tggaccgac ggttctctgg ctacaggcgt ttggcctggg       780
caacgagtgg gggtgtggat ggcccatcga gcagcccaat ttatcctcct acgggaaagc      840 tattccttt acaaaactct acgggataag ctgcagtggg ccggggcgag gttttttgtac      900 gatggtaaca acaaggtcaa ttga                                              924
```

<210> SEQ ID NO 18
<211> LENGTH: 307
<212> TYPE: PRT
<213> ORGANISM: Crocosphaera watsonii

<400> SEQUENCE: 18

```
Met Glu Leu Lys Gln Val Ile Ile Ala His Lys Ala Gly Asp Pro Asp
1               5                   10                  15

Ser Gln Lys Trp Ala Gln Arg Cys Ala Lys Glu Leu Glu Ala Leu Asp
                20                  25                  30

Cys Lys Val Leu Met Gly Pro Ser Gly Tyr Lys Asp Asn Pro Tyr Pro
            35                  40                  45

Val Phe Leu Ser Ser Ala Ser Glu Lys Ile Asp Leu Ala Ile Val Leu
        50                  55                  60

Gly Gly Asp Gly Thr Ile Leu Ala Ser Ala Arg Gln Leu Ala Pro Glu
65                  70                  75                  80

Gly Ile Pro Ile Leu Ala Val Asn Val Gly His Leu Gly Phe Leu
                85                  90                  95

Thr Glu Pro Phe Glu Leu Phe Lys Asp Thr Ala Gln Val Trp His Arg
            100                 105                 110

Leu Gln Ser Asp Arg Tyr Ala Met Leu Gln Arg Met Met Leu Glu Ala
        115                 120                 125

Arg Val Cys Glu Gly Asp Arg Cys Ser Pro Glu Ala Thr Ser Asp Arg
130                 135                 140

Phe Tyr Cys Leu Asn Glu Met Cys Ile Lys Pro Ala Ser Ile Asp Arg
145                 150                 155                 160

Met Pro Thr Ala Ile Leu Glu Leu Glu Val Asp Gly Glu Ile Val Asp
                165                 170                 175

Gln Tyr Gln Gly Asp Gly Leu Leu Val Ala Thr Pro Thr Gly Ser Thr
            180                 185                 190

Cys Tyr Thr Ala Ser Ala Asn Gly Pro Ile Ile His Pro Gly Met Asp
        195                 200                 205

Ala Ile Ala Val Thr Pro Ile Cys Pro Leu Ser Leu Ser Ser Arg Pro
    210                 215                 220

Ile Val Ile Pro Pro Gly Ser Ile Val Asn Ile Trp Pro Leu Gly Asp
225                 230                 235                 240

Tyr Glu Leu Asn Thr Lys Leu Trp Thr Asp Ser Ser Leu Ala Thr Ser
                245                 250                 255

Ile Trp Pro Gly Gln Trp Ile Ser Val Lys Met Ala His Cys Met Ala
```

```
                    260                 265                 270
Arg Phe Ile Val Leu Arg Glu Asn Tyr Ser Phe Tyr Gln Thr Leu Arg
                275                 280                 285

Glu Lys Leu Gln Trp Ala Gly Thr Arg Ile His Phe Asp Asn Asn His
            290                 295                 300

Arg Leu Asn
305

<210> SEQ ID NO 19
<211> LENGTH: 924
<212> TYPE: DNA
<213> ORGANISM: Crocosphaera watsonii

<400> SEQUENCE: 19
gtggaactca aacaagttat catcgcccat aaagcaggag acccggatag tcaaaaatgg      60
gcgcaacgct gcgctaaaga actagaagcc cttgactgta aagtattaat gggaccaagt     120
ggctataaag ataatcctta tcccgtattt ctttcctctg cctcagaaaa aatcgattta     180
gccatcgtct tagggggaga tggcactatt ttagcctctg caagacaatt ggccccagaa     240
ggaattccca ttttagcggt gaatgtgggg ggacatctcg gcttttttaac cgaaccctt     300 gaattattta aggatacggc acaagtatgg catcgtctgc aaagcgatcg ctacgccatg     360
ttacaaagaa tgatgttaga agcgcgggtg tgtgaagggg atcgctgttc ccctgaagca     420
actagcgatc gcttctactg tctcaacgaa atgtgtatta accagctag tattgaccga     480 atgcccactg ctattttgga actagaagtg atggggaaa ttgtagacca atatcaagga     540
gatggcttat tggtagccac tcccacaggt tcaacctgtt acacagcctc ggctaatgga     600
ccaattattc acccaggcat ggacgcgatc gccgttaccc ccatttgtcc tttaagtcta     660
tcgagtcgtc ctattgtcat tcctccaggt tctatagtca atatttggcc tttgggagat     720
tatgaattaa atactaaatt atggactgat agttctttag ccacttctat ttggccgggt     780
caatggatat cggttaaaat ggcccattgt atggctaggt ttattgtctt gcagagaaat     840
tattctttct atcaaaccct acgagaaaag ttacaatggg ctggaactag aattcatttt     900
gataataatc atcggcttaa ttag                                            924

<210> SEQ ID NO 20
<211> LENGTH: 309
<212> TYPE: PRT
<213> ORGANISM: Trichodesmium erythraeum IMS101

<400> SEQUENCE: 20

Met Asp Leu Lys Arg Val Ile Ile Ala His Lys Ala Arg Asp Asp Ile
1               5                   10                  15

Ser Arg Arg Tyr Ala Glu Gln Ser Ala Arg Glu Leu Glu Lys Arg Gly
            20                  25                  30

Cys Arg Val Leu Met Gly Pro Ser Gly Pro Gln Asp Asn Pro Tyr Pro
        35                  40                  45

Val Phe Leu Ala Ser Ser Asn Asn Lys Ile Asp Leu Ala Val Val Leu
    50                  55                  60

Gly Gly Asp Gly Thr Ile Leu Ala Ala Ala Arg Ser Leu Ala Pro Asp
65                  70                  75                  80

Gly Ile Pro Ile Leu Ala Val Asn Val Gly His Leu Gly Phe Leu
                85                  90                  95

Thr His Asn Phe Glu Asp Phe Gln Asp Thr Glu Lys Val Trp Asp Arg
            100                 105                 110
```

Leu Phe Glu Asp Arg Tyr Ala Leu Gln Leu Arg Met Met Leu Gln Ser
            115                 120                 125

Ala Val Phe Asp Gly Asp Arg Tyr Asn Leu Lys Pro Val Ser Asp Asn
        130                 135                 140

Phe Leu Ala Leu Asn Glu Phe Cys Val Lys Pro Ala Ser Ala Asp Arg
145                 150                 155                 160

Met Pro Thr Ser Ile Leu Glu Leu Glu Ile Asp Gly Glu Ile Val Asp
                165                 170                 175

Gln Tyr Gln Gly Asp Gly Leu Ile Val Ala Ser Pro Thr Gly Ser Thr
            180                 185                 190

Cys Tyr Thr Ala Ser Ala Asn Gly Pro Ile Met His Ser Gly Met Ala
        195                 200                 205

Ser Ile Ser Ile Thr Pro Ile Cys Pro Leu Ser Leu Ser Ser Arg Pro
210                 215                 220

Ile Val Leu Pro Pro Gly Cys Val Val Ser Ile Trp Pro Leu His Asp
225                 230                 235                 240

His Asp Leu Ser Thr Lys Leu Trp Ala Asp Gly Val Leu Cys Thr Ser
                245                 250                 255

Ile Trp Pro Gly Lys Arg Val Asn Val Arg Met Ala Asn Cys Gln Ala
            260                 265                 270

Lys Phe Ile Ile Leu Arg Glu Asn Tyr Ser Phe Phe Gln Thr Leu Arg
        275                 280                 285

Glu Lys Leu Leu Trp Ala Gly Ala Arg Ile Lys Tyr Gln Asn Tyr His
    290                 295                 300

Arg Asn Ser Glu Ser
305

<210> SEQ ID NO 21
<211> LENGTH: 930
<212> TYPE: DNA
<213> ORGANISM: Trichodesmium erythraeum

<400> SEQUENCE: 21
tcagctctca ctattccgat ggtagttttg atacttaatt ctagcaccag cccatagtag    60 ttttctctg agagtctgaa aaaatgaata attttcccgc agaataataa acttagcttg   120
acaatttgcc atacgcacat ttactctttt tcctggccat atagaagtac atagaactcc   180
atctgcccag agtttagtac ttagatcgtg atcatgtaaa ggccaaatac taactacaca   240
accaggagga agtacaatag ggcggctcga aagacttaga gggcaaattg gtgttatgga   300
aatggaagcc atgccagagt gcataattgg tccattagca gaggcagtat aacaagtgga   360
gcctgtggga cttgcaacaa ttaatccatc cccttgatat tggtctacta tctcaccatc   420
aatttctagt tctaaaatag aagtaggcat tctgtcagca gaagcaggtt taacgcaaaa   480
ctcatttaag gctaaaaagt tatcgctgac tggtttgagg ttatagcgat cgccatcaaa   540
tactgctgac tgcaacatca ttcttagttg taatgcatag cggtcttcaa ataacctatc   600
ccatactttt tctgtatcct gaaaatcttc aaaattatgg gttaaaaagc ctaaatgtcc   660
tcctacatta actgctaaga taggaattcc atccggtgct aaacttctag ctgcagctaa   720
tattgtacca tctcctccta agactactgc caaatcaatt ttattattgc tagaagcgag   780
aaaaactgga taaggattat cttgtggccc acttgggccc attaagactc gacatcctct   840
cttttccaac tctctcgcag attgttctgc ataacgacgg cttatatcat ctctagcctt   900
atgagcaata attactcgtt taagatccat                                    930

<210> SEQ ID NO 22
<211> LENGTH: 2622
<212> TYPE: DNA
<213> ORGANISM: Synechocystis

<400> SEQUENCE: 22

| | | | | | |
|---|---|---|---|---|---|
| atgaaaattc | ttaaaaccct | taccctccgc | ggccctaact | actggagcat | tcgacgcaag | 60 |
| aagttaattg | taatgcgcct | cgacctggag | gatttggcgg | agcgaccctc | caacagtatt | 120 |
| cctggttttt | atgaagggtt | gatcagggtg | ttgccttctc | ttgtagaaca | tttttgctcc | 180 |
| ccaggacacc | ggggcggctt | tttggcaagg | gtgcgggagg | gaacctatat | ggccatata | 240 |
| gtcgagcatg | tggccctgga | attacaggag | ttggtgggga | tgacggcggg | gtttggtcgc | 300 |
| accagagaaa | cctccacccc | aggcatttat | aacgttgttt | atgaatacgt | agatgaacag | 360 |
| gcaggacgtt | acgctggccg | agccgcggtg | cgcttgtgtc | gttccttggt | ggatacgggg | 420 |
| gattattccc | tgacagaatt | ggaaaaggat | ctggaagatt | tacgggattt | gggcgctaac | 480 |
| tcagccctgg | ggcccagcac | agaaaccatt | gtcactgaag | ccgatgcccg | taaaattccc | 540 |
| tggatgctgc | tcagtgccag | ggccatggtg | caattgggtt | atggggttca | ccaacagaga | 600 |
| attcaggcca | cccttagttc | ccattccggc | attctggggg | ttgaactggc | ctgtgataag | 660 |
| gaaggtacaa | aaaccattct | ccaagatgcg | ggcattcccg | ttccccgggg | caccactatc | 720 |
| caatattttg | atgatttgga | agaagccatc | aatgatgtcg | ggggttatcc | agtggtaatt | 780 |
| aaaccccctgg | acggtaacca | tggtcgggggg | atcaccatca | atgtgcgcca | ttgggaagag | 840 |
| gcgatcgccg | cctatgatct | ggccgctgag | gagtccaaaa | gtcgttccat | tattgtggag | 900 |
| cgttactacg | agggcagtga | ccaccgggtc | ttggtagtca | atggcaagct | agtggcggtg | 960 |
| gcggaaagaa | ttccagccca | tgtaaccggg | gatggcactt | ccaccatcac | tgaattaatt | 1020 |
| gataaaacta | atcaggatcc | caatcgcggc | gatggccatg | ccaacatcct | cactaaaatc | 1080 |
| gtggtcaata | aaacggcgat | cgatgtgatg | aacgccagg | gttataacct | agacagtgtt | 1140 |
| ttacctaagg | atgaagtggt | ttacctgcgg | gccaccgcta | acctcagcac | gggaggcata | 1200 |
| gccattgacc | gcaccgatga | tattcacccg | gaaaatatct | ggttgatgga | aagggtagcc | 1260 |
| aaggtcattg | gcttggacat | tgccggcatt | gacgtggtga | cctccgacat | cagcaagccc | 1320 |
| ctacgggaaa | ccaacggagt | aattgtggaa | gttaacgccg | ctccaggttt | tcgtatgcat | 1380 |
| gtggccccca | gccagggtct | gccccgtaac | gtggccgcac | cagtattgga | tatgctcttt | 1440 |
| ccctccggta | cccccagccg | cattcccatt | ttggccgtga | cggggactaa | tggtaaaacc | 1500 |
| accaccaccc | gcctcttggc | tcacatttat | cggcaaacgg | gcaaaacggt | gggttacacc | 1560 |
| agcaccgatg | ccatttatat | caacgaatac | tgcgtggaaa | aaggcgataa | tacgggggccc | 1620 |
| cagagtgccg | cagtaatttt | gcgggatcct | acggtggagg | tggcagtgtt | agaaacggcc | 1680 |
| cggggaggca | ttttacgggc | aggtcttgct | tttgataccct | gtgacgtggg | ggtagtgctc | 1740 |
| aacgtggcgg | cggatcacct | cggtttggga | gacatcgaca | ccatcgaaca | aatggccaaa | 1800 |
| gttaagtccg | tcattgcaga | ggtggtggac | cccagtggtt | atgcggtgct | caatgcggat | 1860 |
| gatcctttag | tagcggctat | ggcagacaaa | gtgaaagcca | aagtggccta | tttctccatg | 1920 |
| aaccccgata | atcctgttat | ccaaaaccac | atacggcgga | atggcattgc | ggcggtgtat | 1980 |
| gagtctggtt | atgtgtccat | tttgaaggc | tcttggactc | tgcgggtgga | agaggccaca | 2040 |
| ttgattccca | tgaccatggg | ggggatggca | ccgtttatga | ttgccaatgc | cctggcagcc | 2100 |

-continued

```
tgtctggcgg cttttgttaa tggcttagat gttgaagtta ttcgccaagg agtaaggact    2160
ttcaccacct cagcggaaca gaccctgga aggatgaatt tgttcaatct gggtcggtac     2220
catgcactgg tggattacgc ccataacccg gcgggctatc gggccgtggg ggattttgtc    2280
aaaaactggc acggtcaacg ctttggtgtg gtgggaggcc ctggcgatcg ccgagatagt    2340
gatctaattg aactgggaca aattgcggcc caggtatttg accggatcat tgtcaaagaa    2400
gatgatgata acggggccg gagtggggga gaaacagcgg atttaattgt taaaggcatt     2460
ttgcaggaga atcccggcgc ggcctatgag gtaattttgg acgaaactgt agcgttgaat    2520
aaggctttag atcaggtaga ggaaaagggt ttggtggtag tgttccccga aagtgtgagc    2580
aaagccattg agttaattaa agcccgtaaa cccattggtt aa                       2622
```

<210> SEQ ID NO 23
<211> LENGTH: 873
<212> TYPE: PRT
<213> ORGANISM: Synechocystis

<400> SEQUENCE: 23

```
Met Lys Ile Leu Lys Thr Leu Thr Leu Arg Gly Pro Asn Tyr Trp Ser
1               5                   10                  15

Ile Arg Arg Lys Lys Leu Ile Val Met Arg Leu Asp Leu Glu Asp Leu
            20                  25                  30

Ala Glu Arg Pro Ser Asn Ser Ile Pro Gly Phe Tyr Glu Gly Leu Ile
        35                  40                  45

Arg Val Leu Pro Ser Leu Val Glu His Phe Cys Ser Pro Gly His Arg
    50                  55                  60

Gly Gly Phe Leu Ala Arg Val Arg Glu Gly Thr Tyr Met Gly His Ile
65                  70                  75                  80

Val Glu His Val Ala Leu Glu Leu Gln Glu Leu Val Gly Met Thr Ala
                85                  90                  95

Gly Phe Gly Arg Thr Arg Glu Thr Ser Thr Pro Gly Ile Tyr Asn Val
            100                 105                 110

Val Tyr Glu Tyr Val Asp Glu Gln Ala Gly Arg Tyr Ala Gly Arg Ala
        115                 120                 125

Ala Val Arg Leu Cys Arg Ser Leu Val Asp Thr Gly Asp Tyr Ser Leu
    130                 135                 140

Thr Glu Leu Glu Lys Asp Leu Glu Asp Leu Arg Asp Leu Gly Ala Asn
145                 150                 155                 160

Ser Ala Leu Gly Pro Ser Thr Glu Thr Ile Val Thr Glu Ala Asp Ala
                165                 170                 175

Arg Lys Ile Pro Trp Met Leu Leu Ser Ala Arg Ala Met Val Gln Leu
            180                 185                 190

Gly Tyr Gly Val His Gln Gln Arg Ile Gln Ala Thr Leu Ser Ser His
        195                 200                 205

Ser Gly Ile Leu Gly Val Glu Leu Ala Cys Asp Lys Glu Gly Thr Lys
    210                 215                 220

Thr Ile Leu Gln Asp Ala Gly Ile Pro Val Pro Arg Gly Thr Thr Ile
225                 230                 235                 240

Gln Tyr Phe Asp Asp Leu Glu Glu Ala Ile Asn Asp Val Gly Gly Tyr
                245                 250                 255

Pro Val Val Ile Lys Pro Leu Asp Gly Asn His Gly Arg Gly Ile Thr
            260                 265                 270

Ile Asn Val Arg His Trp Glu Glu Ala Ile Ala Ala Tyr Asp Leu Ala
        275                 280                 285
```

-continued

```
Ala Glu Glu Ser Lys Ser Arg Ser Ile Ile Val Arg Tyr Tyr Glu
    290                 295                 300

Gly Ser Asp His Arg Val Leu Val Val Asn Gly Lys Leu Val Ala Val
305                 310                 315                 320

Ala Glu Arg Ile Pro Ala His Val Thr Gly Asp Gly Thr Ser Thr Ile
                325                 330                 335

Thr Glu Leu Ile Asp Lys Thr Asn Gln Asp Pro Asn Arg Gly Asp Gly
            340                 345                 350

His Ala Asn Ile Leu Thr Lys Ile Val Asn Lys Thr Ala Ile Asp
        355                 360                 365

Val Met Glu Arg Gln Gly Tyr Asn Leu Asp Ser Val Leu Pro Lys Asp
    370                 375                 380

Glu Val Val Tyr Leu Arg Ala Thr Ala Asn Leu Ser Thr Gly Gly Ile
385                 390                 395                 400

Ala Ile Asp Arg Thr Asp Asp Ile His Pro Glu Asn Ile Trp Leu Met
                405                 410                 415

Glu Arg Val Ala Lys Val Ile Gly Leu Asp Ile Ala Gly Ile Asp Val
            420                 425                 430

Val Thr Ser Asp Ile Ser Lys Pro Leu Arg Glu Thr Asn Gly Val Ile
        435                 440                 445

Val Glu Val Asn Ala Ala Pro Gly Phe Arg Met His Val Ala Pro Ser
    450                 455                 460

Gln Gly Leu Pro Arg Asn Val Ala Ala Pro Val Leu Asp Met Leu Phe
465                 470                 475                 480

Pro Ser Gly Thr Pro Ser Arg Ile Pro Ile Leu Ala Val Thr Gly Thr
                485                 490                 495

Asn Gly Lys Thr Thr Thr Thr Arg Leu Leu Ala His Ile Tyr Arg Gln
            500                 505                 510

Thr Gly Lys Thr Val Gly Tyr Thr Ser Thr Asp Ala Ile Tyr Ile Asn
        515                 520                 525

Glu Tyr Cys Val Glu Lys Gly Asp Asn Thr Gly Pro Gln Ser Ala Ala
    530                 535                 540

Val Ile Leu Arg Asp Pro Thr Val Glu Val Ala Val Leu Glu Thr Ala
545                 550                 555                 560

Arg Gly Gly Ile Leu Arg Ala Gly Leu Ala Phe Asp Thr Cys Asp Val
                565                 570                 575

Gly Val Val Leu Asn Val Ala Ala Asp His Leu Gly Leu Gly Asp Ile
            580                 585                 590

Asp Thr Ile Glu Gln Met Ala Lys Val Lys Ser Val Ile Ala Glu Val
        595                 600                 605

Val Asp Pro Ser Gly Tyr Ala Val Leu Asn Ala Asp Asp Pro Leu Val
    610                 615                 620

Ala Ala Met Ala Asp Lys Val Lys Ala Lys Val Ala Tyr Phe Ser Met
625                 630                 635                 640

Asn Pro Asp Asn Pro Val Ile Gln Asn His Ile Arg Arg Asn Gly Ile
                645                 650                 655

Ala Ala Val Tyr Glu Ser Gly Tyr Val Ser Ile Leu Glu Gly Ser Trp
            660                 665                 670

Thr Leu Arg Val Glu Glu Ala Thr Leu Ile Pro Met Thr Met Gly Gly
        675                 680                 685

Met Ala Pro Phe Met Ile Ala Asn Ala Leu Ala Ala Cys Leu Ala Ala
    690                 695                 700
```

```
Phe Val Asn Gly Leu Asp Val Glu Val Ile Arg Gln Gly Val Arg Thr
705                 710                 715                 720
Phe Thr Thr Ser Ala Glu Gln Thr Pro Gly Arg Met Asn Leu Phe Asn
                725                 730                 735
Leu Gly Arg Tyr His Ala Leu Val Asp Tyr Ala His Asn Pro Ala Gly
            740                 745                 750
Tyr Arg Ala Val Gly Asp Phe Val Lys Asn Trp His Gly Gln Arg Phe
        755                 760                 765
Gly Val Val Gly Gly Pro Asp Arg Arg Asp Ser Asp Leu Ile Glu
    770                 775                 780
Leu Gly Gln Ile Ala Ala Gln Val Phe Asp Arg Ile Ile Val Lys Glu
785                 790                 795                 800
Asp Asp Asp Lys Arg Gly Arg Ser Gly Gly Glu Thr Ala Asp Leu Ile
                805                 810                 815
Val Lys Gly Ile Leu Gln Glu Asn Pro Gly Ala Ala Tyr Glu Val Ile
            820                 825                 830
Leu Asp Glu Thr Val Ala Leu Asn Lys Ala Leu Asp Gln Val Glu Glu
        835                 840                 845
Lys Gly Leu Val Val Val Phe Pro Glu Ser Val Ser Lys Ala Ile Glu
    850                 855                 860
Leu Ile Lys Ala Arg Lys Pro Ile Gly
865                 870
```

<210> SEQ ID NO 24
<211> LENGTH: 1230
<212> TYPE: DNA
<213> ORGANISM: Synechocystis

<400> SEQUENCE: 24

```
atggccgccc atcccaaccc atggcattgg aaaacaatta tgcgtgatgt ttttattgtt      60
gccgctaaac gaactcccct gggacgtttt ggtggctccc tgaccaattt ttcggcggcg     120
gatttgggag cccatgtgat gaaaagcgtc ctagcccagg ccggggtggg gggagaccag     180
cttgacctgt acattatggg caacgtgtta agggctggcc atgggcaatt gattccccgg     240
caagcggcct tgaaggcgga gattcccgat acggtgacg ttatgcagt ggatatggtc      300
tgctcttccg ccatgatgag tgtgattaat gcagctttaa ccatccgggc tggggagggg     360
gatttaattt tagctggagg gacggaatcc atgtcccaaa ctggttttta cctttcccac     420
cgggcccgct ggggctacaa gttcctcatg ggagcaccgg aaaatttaac cgatctcctg     480
ctccatgatg gtttgacgga cagcaccaat ggggagggca tgggggaaca gacgaaaaaa     540
ttggccgcag agcatggttt cagccggata gaattggacg aagtggcctg cttatcgcaa     600
caaagggcgg cccacgccac ggaatctggt tattttgact cagaaattgc ccgattgaa      660
atcaccagtc ggaaaggaac ccaggtgtta gccagtgatg aaggtattcg cagtgacacc     720
accgtggaaa gtctaggcaa attgcgctcg cctttgccaa aggacggagt gttaacagcg     780
ggcaactgta gtcagattac cgatggggcg gcagctttgc tcctggccag tggggaagcg     840
gtggaaaaat atcaactcaa acccttggca aaattttggg aggcagttg gcggcgggt      900
actcccagtc gttttcctga gttgccatt ccgctagcc agaaactgtt agcaaagcta      960
gataaaaccc tggcagattt tgacttgttt gaaaataatg aagccttctc cgtcagcaat    1020
cttttattg agcggcggtt gggggtggat cgggacaagt tgaatgtgaa cggtggggcg     1080
atcgccctgg ggcatcccat tggagcgtcg ggggccagga tcatggttac cctactctat    1140
```

```
gccttgcaac aacgggataa aactctgggg ttagcagccc tttgccatgg cacggggggc   1200
ggtacggcga tcgccttaga gcgggtgtga                                    1230
```

<210> SEQ ID NO 25
<211> LENGTH: 409
<212> TYPE: PRT
<213> ORGANISM: Synechocystis

<400> SEQUENCE: 25

```
Met Ala Ala His Pro Asn Pro Trp His Trp Lys Thr Ile Met Arg Asp
1               5                   10                  15

Val Phe Ile Val Ala Ala Lys Arg Thr Pro Leu Gly Arg Phe Gly Gly
            20                  25                  30

Ser Leu Thr Asn Phe Ser Ala Ala Asp Leu Gly Ala His Val Met Lys
        35                  40                  45

Ser Val Leu Ala Gln Ala Gly Val Gly Gly Asp Gln Leu Asp Leu Tyr
    50                  55                  60

Ile Met Gly Asn Val Leu Arg Ala Gly His Gly Gln Leu Ile Pro Arg
65                  70                  75                  80

Gln Ala Ala Leu Lys Ala Glu Ile Pro Asp Thr Val Asp Gly Tyr Ala
                85                  90                  95

Val Asp Met Val Cys Ser Ser Ala Met Met Ser Val Ile Asn Ala Ala
            100                 105                 110

Leu Thr Ile Arg Ala Gly Glu Gly Asp Leu Ile Leu Ala Gly Gly Thr
        115                 120                 125

Glu Ser Met Ser Gln Thr Gly Phe Tyr Leu Ser His Arg Ala Arg Trp
    130                 135                 140

Gly Tyr Lys Phe Leu Met Gly Ala Pro Glu Asn Leu Thr Asp Leu Leu
145                 150                 155                 160

Leu His Asp Gly Leu Thr Asp Ser Thr Asn Gly Glu Gly Met Gly Glu
                165                 170                 175

Gln Thr Glu Lys Leu Ala Ala Glu His Gly Phe Ser Arg Ile Glu Leu
            180                 185                 190

Asp Glu Val Ala Cys Leu Ser Gln Gln Arg Ala Ala His Ala Thr Glu
        195                 200                 205

Ser Gly Tyr Phe Asp Ser Glu Ile Ala Pro Ile Glu Ile Thr Ser Arg
    210                 215                 220

Lys Gly Thr Gln Val Leu Ala Ser Asp Glu Gly Ile Arg Ser Asp Thr
225                 230                 235                 240

Thr Val Glu Ser Leu Gly Lys Leu Arg Ser Ala Phe Ala Lys Asp Gly
                245                 250                 255

Val Leu Thr Ala Gly Asn Cys Ser Gln Ile Thr Asp Gly Ala Ala Ala
            260                 265                 270

Leu Leu Leu Ala Ser Gly Glu Ala Val Glu Lys Tyr Gln Leu Lys Pro
        275                 280                 285

Leu Ala Lys Ile Leu Gly Gly Ser Trp Ala Ala Gly Thr Pro Ser Arg
    290                 295                 300

Phe Pro Glu Leu Pro Ile Thr Ala Ser Gln Lys Leu Leu Ala Lys Leu
305                 310                 315                 320

Asp Lys Thr Leu Ala Asp Phe Asp Leu Phe Glu Asn Asn Glu Ala Phe
                325                 330                 335

Ser Val Ser Asn Leu Leu Phe Glu Arg Arg Leu Gly Val Asp Arg Asp
            340                 345                 350

Lys Leu Asn Val Asn Gly Gly Ala Ile Ala Leu Gly His Pro Ile Gly
```

```
                355                 360                 365
Ala Ser Gly Ala Arg Ile Met Val Thr Leu Leu Tyr Ala Leu Gln Gln
        370                 375                 380

Arg Asp Lys Thr Leu Gly Leu Ala Ala Leu Cys His Gly Thr Gly Gly
385                 390                 395                 400

Gly Thr Ala Ile Ala Leu Glu Arg Val
                405

<210> SEQ ID NO 26
<211> LENGTH: 271
<212> TYPE: PRT
<213> ORGANISM: SYNECHOCYSTIS

<400> SEQUENCE: 26

Met Pro Leu Ser Ser Gln Pro Ala Ile Leu Ile Ile Gly Gly Ala Glu
1               5                   10                  15

Asp Lys Val His Gly Arg Glu Ile Leu Gln Thr Phe Trp Ser Arg Ser
                20                  25                  30

Gly Gly Asn Asp Ala Ile Ile Gly Ile Pro Ser Ala Ser Arg Glu
            35                  40                  45

Pro Leu Leu Ile Gly Glu Arg Tyr Gln Thr Ile Phe Ser Asp Met Gly
    50                  55                  60

Val Lys Glu Leu Lys Val Leu Asp Ile Arg Asp Arg Ala Gln Gly Asp
65                  70                  75                  80

Asp Ser Gly Tyr Arg Leu Phe Val Glu Gln Cys Thr Gly Ile Phe Met
                85                  90                  95

Thr Gly Gly Asp Gln Leu Arg Leu Cys Gly Leu Leu Ala Asp Thr Pro
            100                 105                 110

Leu Met Asp Arg Ile Arg Gln Arg Val His Asn Gly Glu Ile Ser Leu
    115                 120                 125

Ala Gly Thr Ser Ala Gly Ala Ala Val Met Gly His His Met Ile Ala
130                 135                 140

Gly Gly Ser Ser Gly Glu Trp Pro Asn Arg Ala Leu Val Asp Met Ala
145                 150                 155                 160

Val Gly Leu Gly Ile Val Pro Glu Ile Val Val Asp Gln His Phe His
                165                 170                 175

Asn Arg Asn Arg Met Ala Arg Leu Leu Ser Ala Ile Ser Thr His Pro
            180                 185                 190

Glu Leu Leu Gly Leu Gly Ile Asp Glu Asp Thr Cys Ala Met Phe Glu
    195                 200                 205

Arg Asp Gly Ser Val Lys Val Ile Gly Gln Gly Thr Val Ser Phe Val
210                 215                 220

Asp Ala Arg Asp Met Ser Tyr Thr Asn Ala Ala Leu Val Gly Ala Asn
225                 230                 235                 240

Ala Pro Leu Ser Leu His Asn Leu Arg Leu Asn Ile Leu Val His Gly
                245                 250                 255

Glu Val Tyr His Gln Val Lys Gln Arg Ala Phe Pro Arg Val Thr
            260                 265                 270

<210> SEQ ID NO 27
<211> LENGTH: 816
<212> TYPE: DNA
<213> ORGANISM: SYNECHOCYSTIS

<400> SEQUENCE: 27
atgcccctat cctcccaacc ggccatctta attattggtg gtgcagaaga taaagttcac      60
```

```
ggccgtgaaa ttttgcaaac cttttggtcg cgttccggtg gcaacgacgc cattattggc      120
atcattccat ctgcatctcg ggagccccta ctgattgggg agagatatca aaccatcttt      180
agcgacatgg gggtcaagga gttaaaagtc ttggacatcc gtgaccgtgc ccagggggat      240
gacagtggct accgattgtt tgtggaacag tgtacaggta ttttcatgac cggggggggat    300 caattgcgtc tctgtggcct gttggcggac actcccctaa tggaccgcat tcgtcagcgg      360
gtacataacg gggaaataag cttagcgggc accagtgcgg gggcggcagt aatgggcat      420 cacatgatcg ccggggggcag tagcggtgaa tggcccaatc gagcgctggt ggatatggcg    480
gtggggctgg gcattgtgcc ggaaattgtg gtggatcagc actttcacaa tcgtaatcgc    540
atggcccggc tgttgagtgc catctctacc catcctgagc tgctgggttt gggtattgat      600
gaagatacct cgccatgtt tgagcgggac ggttccgtta aggtaattgg ccaaggcaca      660
gtctcctttg tcgatgccag ggacatgagc tacactaacg ccgctttggt gggggccaat    720
gccccattga gtctccataa tttgcggctc aatatccttg tccatgggga ggtttatcat     780
caggtaaaac agcgggcctt tccccgggta acctag                                 816

<210> SEQ ID NO 28
<211> LENGTH: 240
<212> TYPE: PRT
<213> ORGANISM: Synechocystis

<400> SEQUENCE: 28
```

Met Leu Ser Leu Gly Leu Glu Asp Lys Val Ile Val Val Thr Gly Gly
1               5                   10                  15

Asn Arg Gly Ile Gly Ala Ala Ile Val Lys Leu Leu Gln Glu Met Gly
            20                  25                  30

Ala Lys Val Ala Phe Thr Asp Leu Ala Thr Asp Gly Gly Asn Thr Glu
        35                  40                  45

Ala Leu Gly Val Val Ala Asn Val Thr Asp Leu Glu Ser Met Thr Ala
    50                  55                  60

Ala Ala Ala Glu Ile Thr Asp Lys Leu Gly Pro Val Tyr Gly Val Val
65                  70                  75                  80

Ala Asn Ala Gly Ile Thr Lys Asp Asn Phe Phe Pro Lys Leu Thr Pro
                85                  90                  95

Ala Asp Trp Asp Ala Val Leu Asn Val Asn Leu Lys Gly Val Ala Tyr
            100                 105                 110

Ser Ile Lys Pro Phe Ile Glu Gly Met Tyr Glu Arg Lys Ala Gly Ser
        115                 120                 125

Ile Val Ala Ile Ser Ser Ile Ser Gly Glu Arg Gly Asn Val Gly Gln
    130                 135                 140

Thr Asn Tyr Ser Ala Thr Lys Ala Gly Val Ile Gly Met Met Lys Ser
145                 150                 155                 160

Leu Ala Arg Glu Gly Ala Arg Tyr Gly Val Arg Ala Asn Ala Val Ala
                165                 170                 175

Pro Gly Phe Ile Asp Thr Glu Met Thr Leu Ala Ile Arg Glu Asp Ile
            180                 185                 190

Arg Glu Lys Ile Thr Lys Glu Ile Pro Phe Arg Arg Phe Gly Lys Pro
        195                 200                 205

Glu Glu Ile Ala Trp Ala Val Ala Phe Leu Leu Ser Pro Val Ala Ser
    210                 215                 220

Ser Tyr Val Thr Gly Glu Val Leu Arg Val Asn Gly Ala His His Thr
225                 230                 235                 240

<210> SEQ ID NO 29
<211> LENGTH: 330
<212> TYPE: PRT
<213> ORGANISM: Synechocystis

<400> SEQUENCE: 29

Met Glu Ser Thr Asn Lys Thr Trp Thr Glu Leu Met Thr Pro Leu Ser
1               5                   10                  15

Gln Phe Trp Leu Glu Ser Ser Gln Ala Trp Lys Asn Trp Phe Asp
            20                  25                  30

Leu Met Ala Lys Gly Gly Ala Gly Ala Met Met Gly Ser Ala Pro Gln
        35                  40                  45

Ser Phe Glu Ser Leu Pro Gln Gln Phe Leu Gln Ser Gln Gln Phe Tyr
    50                  55                  60

Gly Glu Leu Leu Lys Leu Ser Phe Glu Ala Trp Gln Ser Leu Trp Pro
65                  70                  75                  80

Lys Leu Asp Asn Gly Ser Ala Pro Gly Ala Val Gln Gly Tyr Leu Lys
                85                  90                  95

Gln Leu Gln Thr Gln Ile Glu Gln Tyr Thr Ala Thr Thr Gln Ala Leu
            100                 105                 110

Gln Gly Asp Met Asp Gly Leu Trp Gln Cys Tyr Ile Lys Glu Val Gln
        115                 120                 125

Arg Phe Ser Gln Leu Trp Leu Ser Thr Trp Gln Ser Ser Val Ala Pro
    130                 135                 140

Leu Gly Lys Leu Pro Thr Gly Asp Ile His Ala Trp Leu Asp Leu Asn
145                 150                 155                 160

Asn Leu Tyr Gly Asp Ala Leu Tyr Asn Lys Asn Leu Ser Ser Phe Met
                165                 170                 175

Arg Ser Pro Leu Leu Gly Pro Ser Arg Glu Met Asn Gly Lys Leu Leu
            180                 185                 190

Arg Ala Phe Asp Asp Trp Val Lys Leu Ser Gln Ala Met Ala Asp Tyr
        195                 200                 205

Gln Leu Leu Glu Ala Asp Ile Gln Tyr Arg Gly Phe Ala Ala Leu Met
    210                 215                 220

Glu Asp Leu Leu Ala Arg Ala Lys Glu Asp Lys Pro Val Lys Thr Trp
225                 230                 235                 240

Lys Glu Phe Gln Gln Arg Trp Ala Ile Ala Ala Asp Gln Val Phe Glu
                245                 250                 255

Glu Ala Phe Cys Glu Glu Lys Asn Leu Lys Val Arg Gly Lys Phe Ile
            260                 265                 270

Asn Ala Leu Asn Arg Tyr Arg Ile Gln Gln Gln Glu Ile Leu Glu Ala
        275                 280                 285

Trp Leu Lys Met Leu Asn Leu Pro Thr Arg Ser Glu Val Asp Glu Ile
    290                 295                 300

His Gln Thr Ile Tyr Gln Leu Arg Lys Glu Val Lys Ser Leu Lys Lys
305                 310                 315                 320

Arg Leu Gly Glu Thr Glu Ala Asn Pro Gly
                325                 330

<210> SEQ ID NO 30
<211> LENGTH: 378
<212> TYPE: PRT
<213> ORGANISM: Synechocystis

<400> SEQUENCE: 30

```
Met Phe Leu Leu Phe Ile Val His Trp Leu Lys Ile Met Leu Pro
1               5                   10                  15

Phe Phe Ala Gln Val Gly Leu Glu Glu Asn Leu His Glu Thr Leu Asp
                20                  25                  30

Phe Thr Glu Lys Phe Leu Ser Gly Leu Glu Asn Leu Gln Gly Leu Asn
            35                  40                  45

Glu Asp Asp Ile Gln Val Gly Phe Thr Pro Lys Glu Ala Val Tyr Gln
50                  55                  60

Glu Asp Lys Val Ile Leu Tyr Arg Phe Gln Pro Val Val Glu Asn Pro
65                  70                  75                  80

Leu Pro Ile Pro Val Leu Ile Val Tyr Ala Leu Val Asn Arg Pro Tyr
                85                  90                  95

Met Val Asp Leu Gln Glu Gly Arg Ser Leu Val Ala Asn Leu Leu Lys
            100                 105                 110

Leu Gly Leu Asp Val Tyr Leu Ile Asp Trp Gly Tyr Pro Ser Arg Gly
        115                 120                 125

Asp Arg Trp Leu Thr Leu Glu Asp Tyr Leu Ser Gly Tyr Leu Asn Asn
130                 135                 140

Cys Val Asp Ile Ile Cys Gln Arg Ser Gln Glu Lys Ile Thr Leu
145                 150                 155                 160

Leu Gly Val Cys Gln Gly Gly Thr Phe Ser Leu Cys Tyr Ala Ser Leu
                165                 170                 175

Phe Pro Asp Lys Val Lys Asn Leu Val Val Met Val Ala Pro Val Asp
            180                 185                 190

Phe Glu Gln Pro Gly Thr Leu Asn Ala Arg Gly Cys Thr Leu
        195                 200                 205

Gly Ala Glu Ala Val Asp Ile Asp Leu Met Val Asp Ala Met Gly Asn
210                 215                 220

Ile Pro Gly Asp Tyr Leu Asn Leu Glu Phe Leu Met Leu Lys Pro Leu
225                 230                 235                 240

Gln Leu Gly Tyr Gln Lys Tyr Leu Asp Val Pro Asp Ile Met Gly Asp
                245                 250                 255

Glu Ala Lys Leu Leu Asn Phe Leu Arg Met Glu Lys Trp Ile Phe Asp
            260                 265                 270

Ser Pro Asp Gln Ala Gly Glu Thr Tyr Arg Gln Phe Leu Lys Asp Phe
        275                 280                 285

Tyr Gln Gln Asn Lys Leu Ile Lys Gly Glu Val Met Ile Gly Asp Arg
290                 295                 300

Leu Val Asp Leu His Asn Leu Thr Met Pro Ile Leu Asn Leu Tyr Ala
305                 310                 315                 320

Glu Lys Asp His Leu Val Ala Pro Ala Ser Ser Leu Ala Leu Gly Asp
                325                 330                 335

Tyr Leu Pro Glu Asn Cys Asp Tyr Thr Val Gln Ser Phe Pro Val Gly
            340                 345                 350

His Ile Gly Met Tyr Val Ser Gly Lys Val Gln Arg Asp Leu Pro Pro
        355                 360                 365

Ala Ile Ala His Trp Leu Ser Glu Arg Gln
370                 375

<210> SEQ ID NO 31
<211> LENGTH: 723
<212> TYPE: DNA
<213> ORGANISM: Synechocystis
```

<400> SEQUENCE: 31

```
atgttaagtc ttggtttgga agataaagta atcgtggtca ccggcggcaa tcggggcatc    60
ggcgcggcga tcgtgaaatt actccaggaa atgggggcca agtagctttt taccgattta   120
gctacggacg ggggtaatac tgaagccctg ggggtggtgg ccaacgtcac cgatttggaa   180
tccatgacgg cggcggcagc ggaaatcacc gataagctgg gccccgttta cggtgtggtg   240
gccaatgccg gtatcaccaa agacaacttt tcccaaaat taaccccccgc cgattgggat   300
gcagtgttga acgttaactt gaaaggggta gcctacagca ttaagccttt catcgaaggc   360
atgtatgaac ggaaagccgg ctccattgtg gccattagtt ccatctccgg ggagcggggt   420
aacgtcggtc aaactaacta ttccgccact aaagctgggg taattggcat gatgaaatcc   480
ctggctcggg aaggggcccg gtatggagtg cgggccaatg cagtagcccc tggtttcatt   540
gacaccgaaa tgactttggc gatccgggaa gatattcggg aaaaaattac caaggaaatc   600
cccttccgcc gttttggtaa accggaggaa attgcctggg cggtggcctt tttactttcc   660
cccgtagcca gtagctatgt caccggcgaa gtattacggg taaatggggc ccaccacacc   720
taa                                                                 723
```

<210> SEQ ID NO 32
<211> LENGTH: 993
<212> TYPE: DNA
<213> ORGANISM: Synechocystis

<400> SEQUENCE: 32

```
atggaatcga caaataaaac ctggacagaa ctcatgactc ccctcagtca gtttttggctg    60
gagtccagta gccaggcttg gaagaattgg tttgacctca tggccaaggg cggggccggc   120
gccatgatgg gctcggctcc ccagtccttt gagtctttgc cccaacagtt cctccaatcc   180
cagcagtttt atggagagtt acttaagctt tcttttgaag cttggcaaag cctgtggcct   240
aaattggata tggttcggc gccaggggca gtgcagggct acctaaaaca gctacaaacc   300
caaattgagc aatataccgc caccaccca gctctccaag gggacatgga tggtttatgg   360
cagtgttaca tcaaggaagt acaaagattt tcccaactct ggctctccac ctggcagagt   420
agcgtcgccc ccctgggcaa attacccacc ggggacatcc atgcttggtt agatttaaat   480
aatctctacg gcgatgccct ctacaacaaa aacctgagca gttttatgcg atcgcctttg   540
ctggggccca gtcgggaaat gaatggcaaa ttattgcggg cctttgacga ttgggttaag   600
ttatcccagg ccatggcaga ctatcaatta ctggaagcag atattcaata ccggggcttt   660
gctgctttga tggaagattt actggcccgg gctaaggaag ataaacccgt taaaacctgg   720
aaggaatttc aacaacggtg ggcgatcgcc gctgaccaag tgtttgaaga agcttttttgt   780
gaggaaaaaa atctgaaagt acggggcaaa ttcatcaatg ccttgaatcg ttatcgcatt   840
cagcaacagg agattctaga agcatggtta aaaatgctga acctccctac ccgctcagag   900
gtggatgaaa ttcatcaaac catttatcag ttgcggaaag aagttaaaag tttgaaaaaa   960
cgattgggag aaacagaagc aaacccaggc taa                                993
```

<210> SEQ ID NO 33
<211> LENGTH: 1137
<212> TYPE: DNA
<213> ORGANISM: Synechocystis

<400> SEQUENCE: 33

```
atgttttttac tatttttttat cgttcattgg ttaaaaatta tgttgccttt ttttgctcag    60
```

```
gtggggttag aagaaaatct ccatgaaacc ctagatttta ctgaaaaatt tctctctggc    120
ttggaaaatt tgcagggttt gaatgaagat gacatccagg tgggctttac ccccaaagaa    180
gcagtttacc aggaagataa ggttattctt taccgtttcc aaccggtggt ggaaaatccc    240
ttacctatcc cggttttaat tgtttacgcc ctggtaaatc gccccacat ggtggatttg    300 caggaaggac gctccctggt ggccaacctc ctcaaactgg gtttggacgt gtatttaatt    360
gattggggtt atccctcccg gggcgatcgt tggttgaccc tagaagatta tttgtctgga    420
tatttgaaca actgtgtcga tattatttgt caacgctccc agcaagaaaa aattacgttg    480
ttaggagttt gtcaggggggg cacatttagc ctgtgttacg cttctctatt cccggataag    540
gttaaaaatt tggtggtgat ggtggctccg gtggactttg aacaacccgg tactttattg    600
aacgcccggg gaggctgtac cttgggagcc gaagcagtag atattgactt aatggtggat    660
gccatgggca atattccagg ggattatctt aacctagaat ttctcatgct taaacccctg    720
caattaggtt accaaaagta tcttgatgtg cccgatatta tggggatga agcgaaattg    780 ttaaactttc tacgcatgga aaaatggatt tttgatagtc ccgatcaagc gggggaaact    840
taccgtcaat tcctcaagga ttttatcaa caaaataaat tgatcaaagg ggaagtgatg    900
attggcgatc gcctggtgga tctgcataat ttgaccatgc ccatattgaa tttatatgcg    960
gaaaaagacc acttggtggc ccctgcttct tccctagctt tgggggacta tttgccggaa   1020
aactgtgact acaccgtcca atctttcccc gtgggtcata ttggcatgta tgtcagtggt   1080
aaagtacaac gggatctgcc cccggcgatc gcccattggc tatcggaacg acagtga      1137

<210> SEQ ID NO 34
<211> LENGTH: 599
<212> TYPE: DNA
<213> ORGANISM: Synechocystis

<400> SEQUENCE: 34
atgaaaattc ttaaaaccct taccctccgc ggccctaact actggagcat tcgacgcaag     60
aagttaattg taatgcgcct cgacctggag gatttggcgg agcgaccctc caacagtatt    120
cctggttttt atgaagggtt gatcagggtg ttgccttctc ttgtagaaca ttttttgctcc    180 ccaggacacc ggggcggctt tttggcaagg gtgcgggagg gaacctatat gggccatata    240
gtcgagcatg tggccctgga attacaggag ttggtgggga tgacggcggg gtttggtcgc    300
accagagaaa cctccacccc aggcatttat aacgttgttt atgaatacgt agatgaacag    360
gcaggacgtt acgctggccg agccgcggtg cgcttgtgtc gttccttggt ggatacgggg    420
gattattccc tgacagaatt ggaaaaggat ctggaagatt tacgggatt gggcgctaac    480 tcagccctgg ggcccagcac agaaaccatt gtcactgaag ccgatgcccg taaaattccc    540
tggatgctgc tcagtgccag ggccatggtg caattgggtt atggggttca ccaacagag     599

<210> SEQ ID NO 35
<211> LENGTH: 600
<212> TYPE: DNA
<213> ORGANISM: Synechocystis

<400> SEQUENCE: 35
cgggtggaag aggccacatt gattcccatg accatggggg ggatggcacc gtttatgatt     60
gccaatgccc tggcagcctg tctggcggct tttgttaatg gcttagatgt tgaagttatt    120
cgccaaggag taaggacttt caccacctca gcggaacaga cccctggaag gatgaatttg    180
```

| | |
|---|---|
| ttcaatctgg gtcggtacca tgcactggtg gattacgccc ataacccggc gggctatcgg | 240 |
| gccgtggggg attttgtcaa aaactggcac ggtcaacgct ttggtgtggt gggaggccct | 300 |
| ggcgatcgcc gagatagtga tctaattgaa ctgggacaaa ttgcggccca ggtatttgac | 360 |
| cggatcattg tcaaagaaga tgatgataaa cggggccgga gtgggggaga acagcggat | 420 |
| ttaattgtta aaggcatttt gcaggagaat cccggcgcgg cctatgaggt aattttggac | 480 |
| gaaactgtag cgttgaataa ggctttagat caggtagagg aaaagggttt ggtggtagtg | 540 |
| ttccccgaaa gtgtgagcaa agccattgag ttaattaaag cccgtaaacc cattggttaa | 600 |

<210> SEQ ID NO 36
<211> LENGTH: 401
<212> TYPE: DNA
<213> ORGANISM: Synechocystis

<400> SEQUENCE: 36

| | |
|---|---|
| tttacaacag gtctgggacc gggcgatcgc ctgttggcag gaccgggtca aattctatag | 60 |
| ccaggggat ggttccacag tgggcattgt ggtggcccat gatgccatca acaaggtgat | 120 |
| tttggcttat tgttgggtc ttactcccgc tcacttttgg caagttaaac agggtaatgg | 180 |
| cggggtgagc gtcattgact atccccaggg tctagataag ccccccagtta ttcaagccat | 240 |
| taatttgatg ggccatttgg gcacagtgtt ggataaaacc gccgccggag ccctatagtc | 300 |
| ctgtccatag ccaattatcc ccccatttgt tccctaactc ttgtttgcta tgactcactt | 360 |
| tggtttgctc tgtccagcaa cgacgggtca tctcaatacc a | 401 |

<210> SEQ ID NO 37
<211> LENGTH: 25
<212> TYPE: DNA
<213> ORGANISM: Artificial
<220> FEATURE:
<223> OTHER INFORMATION: Synthetic

<400> SEQUENCE: 37

| | |
|---|---|
| ctagaaacgg gaattcaagc ggaat | 25 |

<210> SEQ ID NO 38
<211> LENGTH: 23
<212> TYPE: DNA
<213> ORGANISM: Artificial
<220> FEATURE:
<223> OTHER INFORMATION: Synthetic

<400> SEQUENCE: 38

| | |
|---|---|
| gtttaatagc atgctttgcc agc | 23 |

<210> SEQ ID NO 39
<211> LENGTH: 2147
<212> TYPE: DNA
<213> ORGANISM: Synechocystis

<400> SEQUENCE: 39

| | |
|---|---|
| ctagaaacgg aaattgaagc ggaatatccc ggattattgc aacagtggaa agatgccccc | 60 |
| gccacagtgc agatgccgga agggaaaaat ttacaacagg tctgggaccg ggcgatcgcc | 120 |
| tgttggcagg accgggtcaa attctatagc caggggatg gttccacagt gggcattgtg | 180 |
| gtggcccatg atgccatcaa caaggtgatt ttggcttatt gttgggtct tactcccgct | 240 |
| cacttttggc aagttaaaca gggtaatggc ggggtgagcg tcattgacta tccccagggt | 300 |
| ctagataagc ccccagttat tcaagccatt aatttgatgg gccatttggg cacagtgttg | 360 |

```
gataaaaccg ccgccggagc cctatagtcc tgtccatagc caattatccc cccatttgtt    420
ccctaactct tgtttgctat gactcacttt ggtttgctct gtccagcaac gacgggtcat    480
ctcaatacca tgttgcccct gggtaaggaa ctgcaacagc ggggtcatac tgtgaccatg    540
tttggggtgc tagatgccca agccaaaacc ctagcggccg gtttgaattt tcaggcgatc    600
gccacaacgg aatttcccct gggagcccag gcagaattta tggctgagtt gggcaaactc    660
agtggcatta aagctttgca atacactgtg gccaaaatca cccagaaagc ggcggccttc    720
tttgaggaag cccctggggt catggccaaa gccggtgtgg aagttttatt agttgatcaa    780
gtttcccaag aaggggggcac cattggcgat cgcctgggta ttcccttcat cagtatatgt    840
agcgctgtcg tacttaatcg agagcccacc ataccgccct atgccacccc ttggccatat    900
gatcctagct ggttgggaca attgcggaat cgccttggct atggactttt aaatcgggcc    960
actaaaccga ttacagcgtt aattaatgac tatcgtcagc gttggaattt acccgcccaa   1020
tctagcccca atgaccgtta ttccccacta gcacaaatta gtcagcaacc ggcagcgttt   1080
gaatttcctc gggaatgttt accaagccgt ttccatttca ctggccctt tcacagcaat    1140 gtggggcgag atatagctga ttttccttgg gagcaattga ccgatcagcc cataatttat   1200
gcctcccttg gtactattca aaatcagtta atgagcacct ttaaaatcat tgccgaagcc   1260
tgtatggatt tggatgccca attgattatt tccctggggg gagccaagct agaatcaatg   1320
cccgcactac ctggtaatcc cctcgttgtt aattacgctc cccaactgga acttctgcaa   1380
agaacagccc ttaccattac ccacgctggg ctcaacacca cgttggaatg cctcaataat   1440
gcagtaccca tggtggccat tcccattgcc aatgatcaac cgggagtagc ggccagaatt   1500
gcctgggctg gagtggggga atttattccc ttgagtaaat tgaatacgaa caatctgcgg   1560
gcagcccttg aaaaagtcct cactgaagat tcttataaaa gaaatactct ccagcttcaa   1620
caagcaatta aaactgctgg aggtcttact aaagcggcgg atattattga gcaggtaaca   1680
gcggaggcca tgggctaaat tttgcaggtt tcaacattgg gaaatcttgt ctctttacaa   1740
cgaagaattt gatatgggta agaatttcaa gaaatatttt aaagttcacc ccaggaacat   1800
taccgccgtc taaaactatt tgccccaaat cattttcagg gcaatgacta acattgctcc   1860
cccaaaaatc cgccccagta attcgttaga aatattggtg gctaccctag cgccaaacaa   1920
actaccaagc acaaatccca ggcaaattag taccgccact ttgatgtcca cgtcccccctt  1980 ttggtagtag gtccaggccg ccgctaaacc aatgggaggc accatgaggg cgagggtggt   2040
gccctgggct aaatgttggc taaaaccaaa accgaatact agcactggca caatgatcaa   2100
tccaccgccg ataccaatca ggccgctggc aaagccggct attaaac                 2147
```